(12) United States Patent
Yamashita et al.

(10) Patent No.: US 9,913,582 B2
(45) Date of Patent: *Mar. 13, 2018

(54) BIOLOGICAL INFORMATION DETECTOR, BIOLOGICAL INFORMATION MEASURING DEVICE, AND METHOD FOR DESIGNING REFLECTING PART IN BIOLOGICAL INFORMATION DETECTOR

(71) Applicant: SEIKO EPSON CORPORATION, Tokyo (JP)

(72) Inventors: Hideto Yamashita, Nagano (JP); Yoshitaka Iijima, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/966,824

(22) Filed: Dec. 11, 2015

(65) Prior Publication Data

US 2016/0095519 A1   Apr. 7, 2016

Related U.S. Application Data

(63) Continuation of application No. 14/520,896, filed on Oct. 22, 2014, now Pat. No. 9,241,644, which is a (Continued)

(30) Foreign Application Priority Data

Feb. 4, 2010   (JP) ................................. 2010-022836

(51) Int. Cl.
  *G01N 21/55* (2014.01)
  *A61B 5/00* (2006.01)
  (Continued)

(52) U.S. Cl.
  CPC ........ *A61B 5/0059* (2013.01); *A61B 5/02055* (2013.01); *A61B 5/02427* (2013.01);
  (Continued)

(58) Field of Classification Search
  USPC ............ 356/445–448; 250/574; 385/37, 115, 385/116, 120, 129, 130
  See application file for complete search history.

(56) References Cited

U.S. PATENT DOCUMENTS 4,078,858 A   3/1978  Mast
5,023,053 A   6/1991  Finlan
(Continued)

FOREIGN PATENT DOCUMENTS

EP   0095759 A1   12/1983
EP   2340764 A1   7/2011
(Continued)

OTHER PUBLICATIONS

Extended European Search Report dated Jun. 7, 2011 for the corresponding European Patent Application No. 11153023.4.

*Primary Examiner* — Tri T Ton
(74) *Attorney, Agent, or Firm* — Global IP Counselors, LLP

(57) ABSTRACT

A biological information detector includes a wristband, a housing, an opening, a light-emitting part, a reflecting part, a light-receiving part, and a protecting part. The opening is defined in a surface of the housing adapted to face a surface of the wrist of the user. The light-emitting part is disposed inside the housing and configured to emit green light. The reflecting part is disposed in periphery of the light emitting part, and configured to reflect the light emitted by the light-emitting part, wherein the reflecting part is disposed inside the housing. The light-receiving part is disposed inside the housing, and configured to receive reflected light reflected at a detection site of the wrist of the user. The protecting part is configured to protect the light-emitting part and the reflecting part, and is disposed at the opening of the housing to contact with the detection site.

9 Claims, 23 Drawing Sheets

Related U.S. Application Data continuation of application No. 14/304,106, filed on Jun. 13, 2014, now Pat. No. 9,179,848, which is a continuation of application No. 13/015,210, filed on Jan. 27, 2011, now Pat. No. 8,823,944.

(51) Int. Cl.

| | | |
|---|---|---|
| *A61B 5/024* | (2006.01) | |
| *A61B 5/1455* | (2006.01) | |
| *G01N 21/47* | (2006.01) | |
| *G01N 21/49* | (2006.01) | |
| *A61B 5/0205* | (2006.01) | |

(52) U.S. Cl.
CPC ...... *A61B 5/02438* (2013.01); *A61B 5/02444* (2013.01); *A61B 5/14552* (2013.01); *A61B 5/681* (2013.01); *A61B 5/7278* (2013.01); *G01N 21/474* (2013.01); *G01N 21/49* (2013.01); *A61B 2562/0219* (2013.01); *A61B 2562/0238* (2013.01); *G01N 2201/064* (2013.01)

(56) References Cited

U.S. PATENT DOCUMENTS

| | | | |
|---|---|---|---|
| 7,034,694 | B2 | 4/2006 | Yamaguchi et al. |
| 9,241,644 | B2 * | 1/2016 | Yamashita ......... A61B 5/02427 |
| 2008/0004510 | A1 * | 1/2008 | Tanzawa ............. A44C 5/0015 |
| | | | 600/301 |
| 2008/0097221 | A1 | 4/2008 | Florian |
| 2009/0310135 | A1 | 12/2009 | Bockstaele et al. |
| 2010/0067015 | A1 | 3/2010 | Matsushita et al. |

FOREIGN PATENT DOCUMENTS

| | | |
|---|---|---|
| JP | 2004-337605 A | 12/2004 |
| JP | 2005-181157 A | 7/2005 |
| WO | 2005/010568 A2 | 2/2005 |
| WO | 2008/040735 A1 | 4/2008 |

* cited by examiner

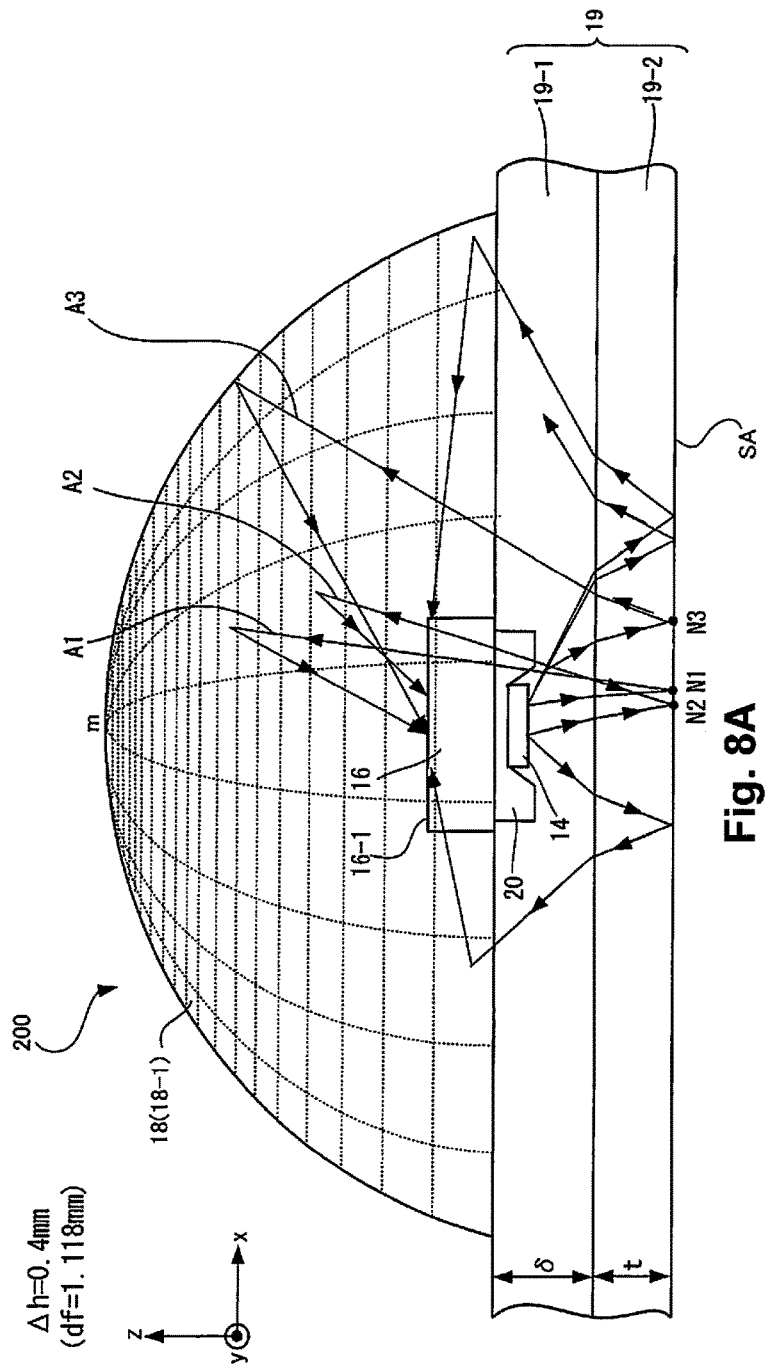
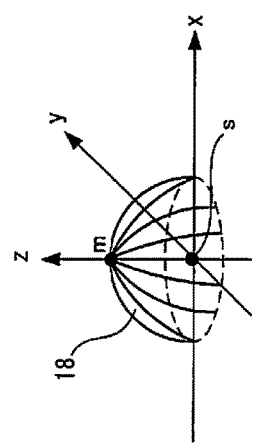
Fig. 8A
Fig. 8B

BIOLOGICAL INFORMATION DETECTOR, BIOLOGICAL INFORMATION MEASURING DEVICE, AND METHOD FOR DESIGNING REFLECTING PART IN BIOLOGICAL INFORMATION DETECTOR

CROSS-REFERENCE TO RELATED APPLICATIONS

This application is a continuation application of U.S. application Ser. No. 14/520,896 filed on Oct. 22, 2014, which is a continuation application of U.S. application Ser. No. 14/304,106 filed on Jun. 13, 2014, which is a continuation application of U.S. application Ser. No. 13/015,210 filed on Jan. 27, 2011, now U.S. Pat. No. 8,823,944. This application claims priority to Japanese Application No. 2010-0022836 filed on Feb. 4, 2010. The entire disclosures of U.S. application Ser. Nos. 14/520,896, 14/304,106 and 13/015,210 and Japanese Application No. 2010-0022836 are hereby incorporated herein by reference.

BACKGROUND

Technological Field

The present invention relates to a biological information detector, a biological information measuring device, and method for designing a reflecting part in the biological information detector and the like.

Background Technology

A biological information measuring device measures human biological information such as, for example, pulse rate, blood oxygen saturation level, body temperature, or heart rate, and an example of a biological information measuring device is a pulse rate monitor for measuring the pulse rate. Also, a biological information measuring device such as a pulse rate monitor may be installed in a clock, a mobile phone, a pager, a PC, or another electrical device, or may be combined with the electrical device. The biological information measuring device has a biological information detector for detecting biological information, and the biological information detector includes a light-emitting part for emitting light towards a detection site (e.g., finger or arm) of a test subject (e.g., a user), and a light-receiving part for receiving light having biological information from the detection site.

There is disclosed in Japanese Laid-Open Publication No. 2004-337605 a reflection-type light sensor in which a light-emitting element and a light-receiving element are coaxially provided. The reflection-type light sensor described in Japanese Laid-Open Publication No. 2004-337605 is designed so that the detection sensitivity of the light-receiving element is at a maximum when a detection target (e.g., a finger) is positioned at a predetermined distance away from a window for transmitting light emitted from the light-emitting element. In paragraph [0032] in Japanese Laid-Open Publication No. 2004-337605, it is disclosed that the emission angle of the light-emitting element can be changed, the size of a substrate can be changed, and the curvature or focal point of a reflecting surface can be changed, in order to set a peak position at which the detection accuracy is at a maximum.

Light emitted by the light-emitting element illuminates a detection site of a test subject via a light-transmitting member (corresponding to a window part in Japanese Laid-Open Publication No. 2004-337605). A part of the light emitted by the light-emitting element is reflected on a surface (and a vicinity of the surface) of the light-transmitting member. The reflected light is light that has been reflected directly on the surface (and a vicinity of the surface) of the light-transmitting member (i.e., directly reflected light), and directly reflected light is invalid light that does not have biological information (i.e., noise light). In an instance in which the directly reflected light (i.e., invalid light) is incident on a light-receiving region of the light-receiving element, the S/N (i.e., signal-to-noise ratio) of a biological information detection signal outputted from the light-receiving element decreases. In order to improve the measurement sensitivity of a biological information measuring device, it is important to design a light-collecting optical system (i.e., a reflecting part) so as to minimize incidence of directly reflected light (i.e., invalid light) on the light-receiving region of the light-receiving element. Merely adjusting the focal length of the reflecting surface as with Patent Citation 1, for example, does not remove the effect of reflected light that has been reflected on a surface side of the light-transmitting member (i.e., the window part), i.e., the effect of directly reflected light (e.g., a decrease in the S/N of the detection signal outputted from the light-receiving element).

SUMMARY

A biological information detector according to one aspect includes a wristband, a housing, an opening, a light-emitting part, a reflecting part, a light-receiving part, and a protecting part. The wristband is adapted to be attached to a wrist of a user. The housing is connected to the wristband and adapted to be placed on the wrist of the user. The opening is defined in a surface of the housing adapted to face a surface of the wrist of the user. The light-emitting part is disposed inside the housing and configured to emit green light. The reflecting part is disposed in periphery of the light emitting part, and configured to reflect the light emitted by the light-emitting part, wherein the reflecting part being disposed inside the housing. The light-receiving part is disposed inside the housing, and configured to receive reflected light reflected at a detection site of the wrist of the user. The protecting part is configured to protect the light-emitting part and the reflecting part, and is disposed at the opening of the housing to contact with the detection site.

BRIEF DESCRIPTION OF THE DRAWINGS

FIG. 8A is a drawing used to describe a behavior of directly reflected light in an instance in which df=1.18 mm (Δh=0.4 m);

FIG. 8B is a drawing used to describe the behavior of directly reflected light in the instance in which df=1.18 mm (Δh=0.4 m);

DESCRIPTION OF EXEMPLARY EMBODIMENTS

Preferred Embodiments of the Invention

A description shall now be given for the present embodiment. The present embodiment described below is not intended to unduly limit the scope of the claims of the present embodiment. Not every configuration described in the present embodiment is necessarily an indispensible constituent feature of the invention.

First Embodiment

First, a description will be given for an overview of a configuration of the biological information detector and the biological information measuring device, examples of behavior of light emitted by the light-emitting part, and other details.

Overview of Configuration of Biological Information Detector, and Other Details

Figure 1A:
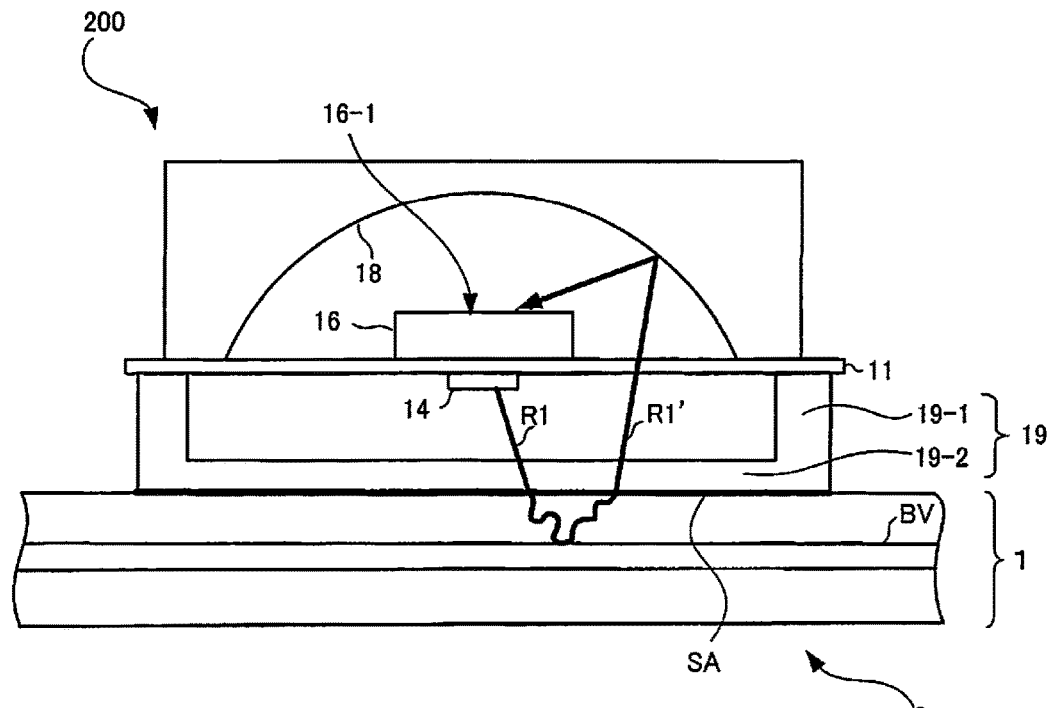
FIG. 1A is a drawing used to represent an example of a configuration of a biological information detector and a preferable design for a reflecting part.
Figure 1B:
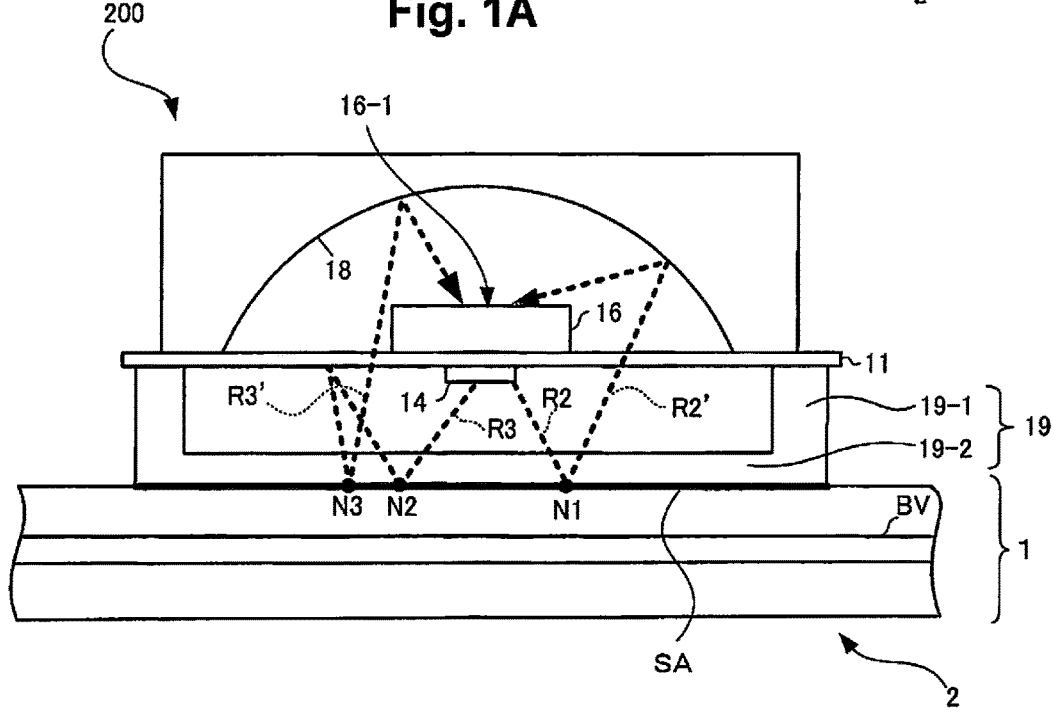
FIG. 1B is the drawing used to represent an example of the configuration of the biological information detector and a preferable design for the reflecting part.

FIGS. 1A and 1B are drawings used to describe an example of a configuration of a biological information detector and a preferable design for a reflecting part. FIG. 1A shows a state in which reflected light (i.e., valid light) is incident on a light-receiving region of a light-receiving part. FIG. 1B shows a state in which light reflected on a contact-surface side of a contact member forming a protecting part (i.e., directly reflected light; invalid light) is incident on the light-receiving region of the light-receiving part. The structure of the biological information detector 200 shown in FIGS. 1A and 1B is identical, and parts that are the same in each drawing are affixed with the same reference numerals.

A configuration of the biological information detector 200 will now be described. The biological information detector 200 can be installed in, e.g., a pulse rate monitor that can be fitted onto a wrist of a person using a wristband or another component (and is not limited to the description given above). Other than pulse rate information (i.e., heart rate information), the biological information may also be blood oxygen saturation, body temperature, or another variable.

As shown in FIGS. 1A and 1B, the biological information detector has: a light-emitting part 14 (with an LED or another light-emitting element) for emitting light R1 directed at a detection site 1 (e.g., finger, arm, or wrist) of a test subject 2 (e.g., a human body); a light-receiving part 16 (with a photodiode or another light-receiving element) for receiving light R1' having biological information produced by the light R1 emitted by the light-emitting part 14 being reflected at a blood vessel BV, which is a biological information source at the detection site 1; a reflecting part 18 for reflecting light having biological information; a protecting part 19; and a light-transmitting substrate 11.

The light-receiving part 16 has a light-receiving region (i.e., light-receiving surface) 16-1 on a side towards the reflecting part 18. The reflecting part 18 has a reflecting surface (i.e., a reflecting mirror) that is a quadric surface. The reflecting surface can be provided on an inner surface of a dome provided on a light path between the light-emitting part 14 and the light-receiving part 16. For example, a main body of the reflecting part 18 is made of a resin, and the inner surface (i.e., a quadric surface formed on a side towards the light-receiving part 16) of the main body is subjected to mirror surface finishing (e.g., a metal film or a similar structure is formed on the surface), thereby making it possible to form the reflecting part (i.e., a reflecting optical system).

The protecting part 19 has a contact member 19-2 provided with a contact surface SA in contact with (or at least has a possibility of being in contact with) the test subject (i.e., measurement target, e.g., a human body), and a spacer member 19-1. The contact member 19-2 and the spacer member 19-1 is formed from a material that is transparent with respect to a wavelength of light R1 emitted by the light-emitting part 14 (e.g., glass). Specifically, the contact member 19-2 is a light-transmitting member. The protecting part 19 is also an accommodating part for accommodating the light-emitting part 14 (i.e., an accommodating container or a protective case), and has a function of protecting the light-emitting part 14.

The substrate 11 is arranged between the reflecting part 18 and the protecting part 19. The substrate 11 has two main surfaces. In the present specification, a main surface of the substrate 11 on a side towards the light-emitting part 14 may be referred to as a first surface (or a reverse surface), and a main surface of the substrate 11 on a side towards the reflecting part 18 may be referred to as a second surface (or a front surface). The light-emitting part 14 is arranged on the first surface (i.e., the reverse surface) of the substrate 11, and the light-receiving part 16 is arranged on the second surface (i.e., the front surface). The light-emitting part 14 and the light-receiving part 16 have an overlap with respect to the plan view. A surface of the light-emitting part 14 that is in contact with the substrate 11 and a surface of the light-receiving part 16 that is in contact with the substrate 11 face each other so as to be separated by a distance equal to the thickness of the substrate 11. The substrate 11 is formed from a material that is transparent with respect to the wavelength of light emitted by the light-emitting part 14 (e.g., polyimide or polyarylate). Specifically, the substrate 11 is a light-transmitting substrate.

Since the substrate 11 is arranged between the reflecting part 18 and the protecting part 19, even in an instance in which the light-emitting part 14 and the light-receiving part 16 are arranged on the substrate 11, there is no need to separately provide a mechanism for supporting the substrate 11 itself, and the number of components is smaller. Also, since the substrate 11 is formed from a material that is transparent with respect to the emission wavelength, the substrate 11 can be disposed on a light path from the light-emitting part 14 to the light-receiving part 16. Therefore, there is no need to accommodate the substrate 11 at a position away from the light path, such as in an interior of the reflecting part 18. A biological information detector that can be readily assembled can thus be provided. Also, the reflecting part 18 makes it possible to increase the amount of light incident on the light-receiving part 16, thereby increasing the detection accuracy (i.e., signal-to-noise ratio) of the biological information detector. The biological information source (e.g., the blood vessel BV) may be near the contact surface SA.

Example of Behavior of Light Emitted by the Light-Emitting Part

Next, a description will be given for an example of behavior of reflected light having biological information, with reference to FIG. 1A. The blood vessel BV, which is a biological information source, is located, e.g., within an interior of the detection site 1 (e.g., a finger or an arm (or in a narrower sense, the wrist)) of the test subject 2 (e.g., a human body). Light R1 emitted by the light-emitting part 14 (specifically, a main light beam, i.e., an expression meaning light that does not contain reflected light reflected on another member) travels into the interior of the detection site 1 and diffuses or scatters at the epidermis, the dermis, and the subcutaneous tissue. The light R1 subsequently reaches the blood vessel BV, which is the biological information source, and is reflected at the blood vessel BV. A part of the light R1 is absorbed by the blood vessel BV. Due to an effect of the pulse, the rate of absorption at the blood vessel BV varies, and the amount of reflected light R1' reflected at the blood vessel BV therefore varies. Therefore, biological information (e.g., pulse rate) is thus reflected in the reflected light R1' reflected at the blood vessel BV.

The reflected light R1' reflected at the blood vessel BV diffuses or scatters at the epidermis, the dermis, and the subcutaneous tissue. In the example shown in FIG. 1A, the reflected light R1' passes through the substrate 11, is reflected on the reflecting part 18, and is directly incident on a light-receiving region (i.e., light-receiving surface) 16-1 of the light-receiving part 16. The expression "is directly incident on" is used to express the fact that the light is not routed via, e.g., a complex reflection process, but via, e.g., a smallest possible number of reflections (i.e., via a simple path). A biological information detection signal outputted by the light-receiving part 16 includes a pulsating component corresponding to the pulse. Therefore, the pulse rate can be measured according to the detection signal.

Next, a description will be given for an example of behavior of reflected light (i.e., invalid light) reflected on a side of the contact member 19-2 forming the protecting part 19 towards the contact surface SA (i.e., at the contact surface SA and a vicinity of the contact surface SA (including an interface between the contact surface and the detection site, as well as the skin surface and an inner side of the skin)) with reference to FIG. 1B. In FIG. 1B, a main light beam R2 emitted by the light-emitting part 14 reflects once at a point N1 on the contact member 19-2 on a side towards the contact surface SA (e.g., at a point on the contact surface SA). A reflected light R2' which has reflected once (i.e., a once-reflected light) passes through the substrate 11, reflects again at the reflecting part 18, and is incident on the light-receiving region 16-1 of the light-receiving part 16.

A main light beam R3 emitted by the light-emitting part 14 reflects twice at positions N2 and N3 on the contact member 19-2 on a side towards the contact surface SA (e.g., at points on the contact surface SA). A reflected light R3' which has reflected twice (i.e., a twice-reflected light) passes through the substrate 11, reflects again at the reflecting part 18, and is incident on the light-receiving region 16-1 of the light-receiving part 16.

The reflected light R2' and the reflected light R3' are reflected lights produced by the light emitted by the light-emitting part 14 directly reflecting on the surface (or a vicinity thereof) of the contact member 19-2, which is a light-transmitting member (i.e., directly reflected light). The directly reflected light is an invalid light (i.e., noise light) that does not have biological information. When the invalid light that does not have biological information is incident on the light-receiving region 16-1 of the light-receiving part 16, the S/N (i.e., signal-to-noise ratio) of the biological information detection signal outputted from the light-receiving part 16 decreases. In order to improve the detection accuracy of the biological information detector (i.e., to improve the measurement accuracy of the biological information measuring device), it is important to design the reflecting part 18, which is a light-collecting optical system, so that directly reflected light (i.e., invalid light) can be inhibited from being incident on the light-receiving region 16-1 of the light-receiving part 16.

Figure 2:
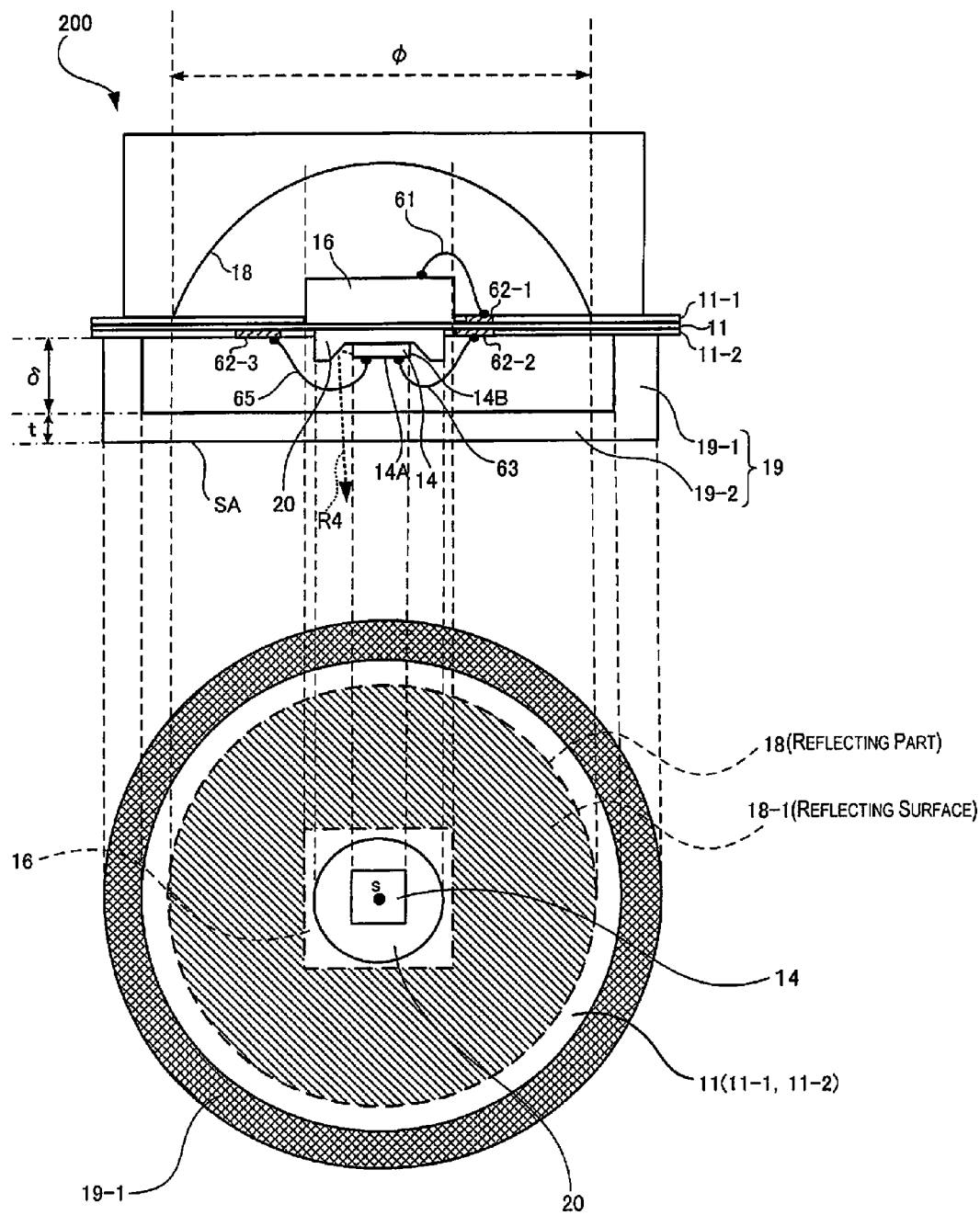
FIG. 2 is a drawing representing a specific example of a configuration of the biological information detector.

Specific Example of a Configuration of the Biological Information Detector, and Example of a Configuration of the Biological Information Measuring Device FIG. 2 is a drawing representing a specific example of a configuration of the biological information detector. The upper side of FIG. 2 shows an example of a cross-section structure of the biological information detector, and the lower side shows positional relationships between each part with respect to the plan view. Parts in FIG. 2 that are the same as those in FIGS. 1A and 1B are affixed with the same reference numerals (this also applies to other drawings described further below).

As shown in FIG. 2, the aperture diameter of the reflecting part 18 is cp. A reflecting surface 18-1 of the reflecting part 18 includes a part of a quadric surface (a spherical surface in this instance; the reflecting surface 18-1 may be, e.g., a substantially hemispherical surface). A bottom part of the hemispherical surface is open, not accounting for the substrate or other components. The shape of the opening with respect to the plan view (i.e., the outer circumferential shape of the reflecting surface with respect to the plan view) is circular as shown in the lower side of FIG. 2, and the diameter (i.e., the aperture diameter) is cp.

The height of the spacer member 19-1 in the protecting part 19 (may be regarded as a spacing between the substrate 11 and a surface of the contact member 19-2 that is opposite the contact surface SA) is δ, and the thickness of the contact member 19-2 is t.

As shown in the lower side of FIG. 2, the light-emitting part 14 and the light-receiving part 16 have an overlap with respect to the plan view. The circumferential shape of each of the light-emitting part 14, the light-receiving part 16, and the reflecting part 18 is a circle, each of which circles being concentric with one another (with the center being represented by s).

The substrate 11 is an optical component as a light-transmitting member, and is also a circuit substrate for forming a circuit. The substrate 11 is, e.g., a printed circuit board. As shown in the upper side of FIG. 2, a wiring 62-1 for the light-receiving part 16 is formed on the first surface (i.e., front surface) of the substrate 11, and wiring 62-2, 62-3 for the light-emitting part 14 are formed on the second surface (i.e., reverse surface) of the substrate 11. The wiring 62-1 and the light-receiving part 16 are connected by a bonding wire 63. The wiring 62-2 and the light-emitting part 14 are connected by a bonding wire 62. The wiring 62-3 and the light-emitting part 14 are connected by a bonding wire 65.

In a printed circuit board, the first surface (i.e., reverse surface) and the second surface (i.e., front surface) are preferably roughened to a certain extent to prevent printed wiring from detaching. However, when the first surface and the second surface of the substrate 11 are roughed, a problem is presented in that scattering of light increases. Therefore, in the example shown in FIG. 2, a light-transmitting film 11-1 and a light-transmitting film 11-2 are respectively formed on the first surface (i.e., reverse surface) and the second surface (i.e., front surface) in a light-transmitting region (or a region excluding a light-blocking region on which wiring or other components are formed) of the substrate 11. The light-transmitting films 11-1 and 11-2 are, e.g., a light-transmitting resist film. Forming the light-transmitting films 11-1 and 11-2 in the light-transmitting region of the substrate 11 smoothens the roughness on each of the reverse surface and the front surface and reduces a difference in refractive index between the substrate 11 and air. Light is thereby inhibited from scattering at the front surface and the reverse surface of the substrate 11 (in a broader sense, including the 11-1 and the 11-2). Also, since the difference in the refraction index between the substrate 11 and air is smaller, the degree to which light refracts in the substrate 11 can be reduced. For example, if the substrate 11 is set to a small thickness, light can be considered to travel straight through the substrate 11 without any significant refraction. This contributes towards making it possible to readily simulate the behavior of light, and to readily design an optical system in the biological information detector 200.

In the example shown in FIG. 2, a reflector 20 is provided. In an instance in which the reflector 20 is referred to as a first reflecting part, the reflecting part 18 having the reflecting surface 18-1 including the quadric surface can be referred to as a second reflecting part.

The reflector 20 has an effect of minimizing a spread of light emitted from the light-emitting part 14, increasing the directivity of light, and reducing the amount of invalid light emitted in a direction other than towards the detection site 1. The light-emitting part 14 has a first light-emitting surface 14A and a second light-emitting surface (i.e., a side surface) 14B, and light is also emitted from the second light-emitting surface 14B. A protruding part (having, on an inner wall surface of which, a reflecting surface that is an inclined or a curved surface) provided on a periphery of the reflector 20 has an effect of reflecting light emitted from a side surface (i.e., the second light-emitting surface 14B) of the light-emitting part 14 (producing a reflected light R4) and directing the light R4 towards the detection site 1.

The reflector 20 has a certain amount of width. Therefore, the reflector 20 also has an effect of preventing a part of the directly reflected light (i.e., invalid light) reflected on a vicinity of the contact surface SA of the contact member 19-2 of the protecting part 19 from entering a side towards the reflecting part 18. For example, directly reflected light incident from diagonally below is reflected on an end part and other parts of the reflector 20, and the directly reflected light is thereby prevented from entering the side towards the reflecting part 18. The reflector 20 also has an effect of reflecting a part of the directly reflected light towards the detection site 1, thereby converting invalid light into valid light.

The effect of improving the S/N due to the preferable reflective characteristics of the reflecting optical system that are realized by the invention is thus supplemented with the effect of improving the S/N due to the reflector 20, and the detection accuracy of the information detector 200 is thereby further improved.

Figure 3:
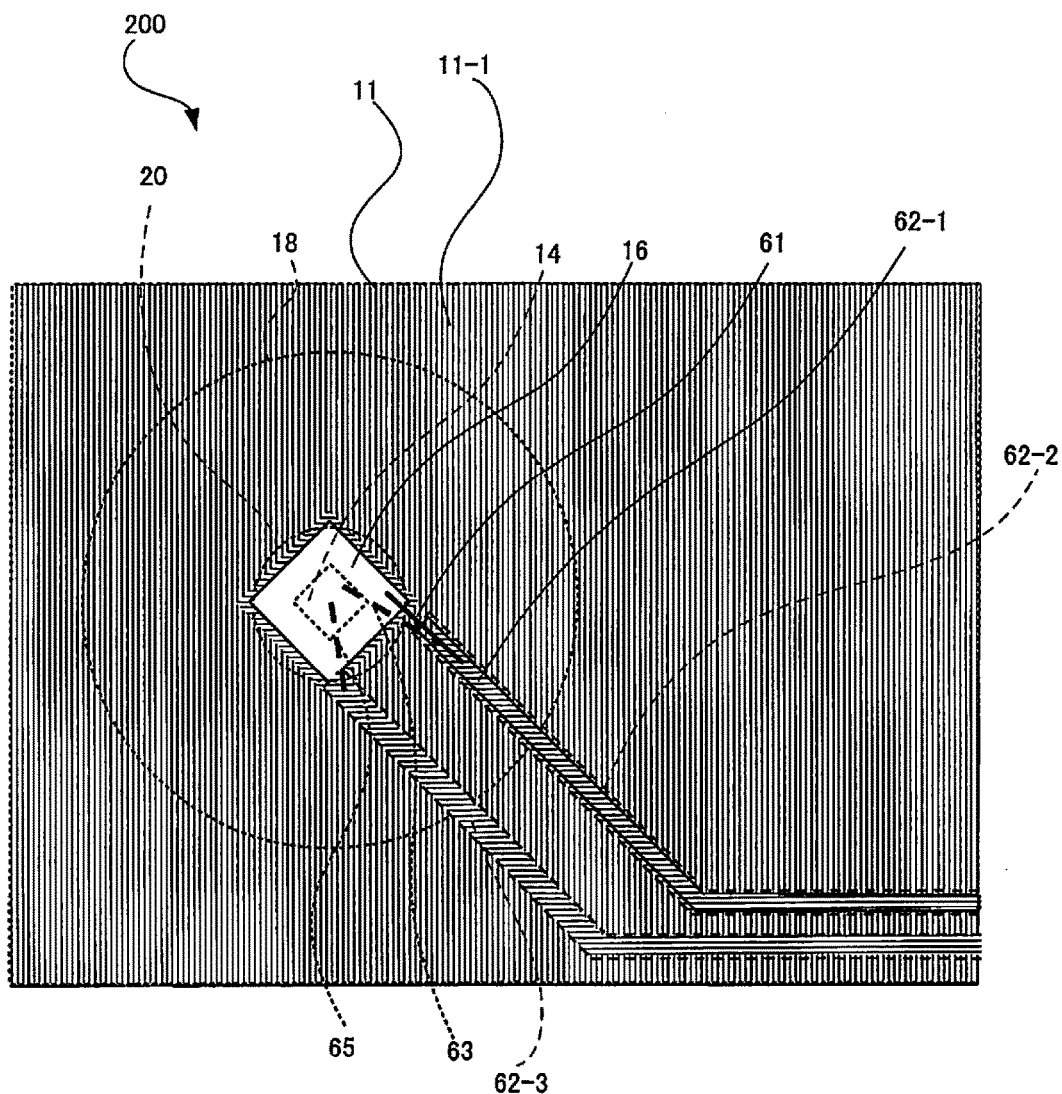
FIG. 3 is a drawing representing, with respect to the plan view, an outer appearance of a substrate coated with a light-transmitting film.

FIG. 3 is a drawing representing, with respect to the plan view, an outer appearance of the substrate coated with the light-transmitting film. FIG. 3 shows an outer appearance of the first surface (i.e., the front surface; the surface on the side towards the light-receiving part 16) of the substrate 11 with respect to the plan view. The light-transmitting film 11-1 is formed on a light-transmitting region (i.e., a region other than a light-blocking region) on the first surface of the substrate 11. The light-transmitting film 11-2 is formed on a light-transmitting region (i.e., a region other than a light-blocking region) is formed on the second surface (i.e., the surface on the side towards the light-emitting part 14).

Figure 4A:
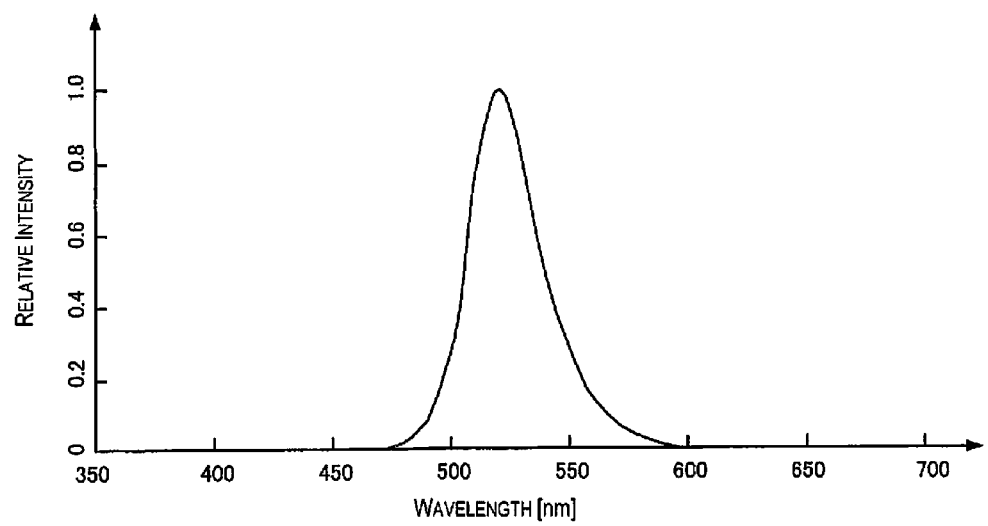
FIG. 4A is a drawing representing an example of intensity characteristics of light emitted by a light-emitting part and an example of sensitivity characteristics of a light-receiving part.
Figure 4B:
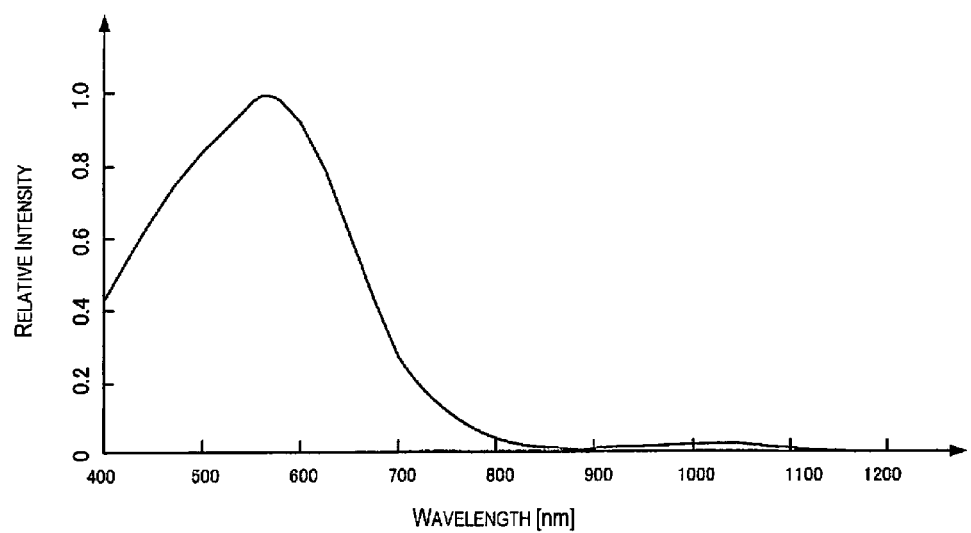
FIG. 4B is a drawing representing an example of the intensity characteristics of light emitted by the light-emitting part and an example of the sensitivity characteristics of the light-receiving part.

FIGS. 4A and 4B are drawings representing an example of intensity characteristics of light emitted by the light-emitting part and an example of sensitivity characteristics of the light-receiving part. In the example of emission intensity characteristics shown in FIG. 4A, the intensity is at a maximum for light having a wavelength of 520 nm, and the intensity of light having other wavelengths is normalized with respect thereto. Also, the wavelengths of light emitted by the light-emitting part 14 are within a range of 470 nm to 600 nm. The light-emitting part 14 includes, e.g., an LED. The light emitted by the LED has a maximum intensity (or in a broader sense, a peak intensity) within a wavelength range of, e.g., 425 nm to 625 nm, and light emitted by the light-emitting part 14 is, e.g., green in color.

FIG. 4B shows an example of sensitivity characteristics of the light-receiving part. A gallium arsenide phosphide photodiode or a silicon photodiode are examples of the light-receiving part 16 that can be used. However, the gallium arsenide phosphide photodiode has a maximum sensitivity (or in a broader sense, a peak sensitivity) for received light having a wavelength within a range of, e.g., 550 nm to 650 nm. Since biological substances (water or hemoglobin) readily allow transmission of infrared light within a wavelength range of 700 nm to 1100 nm, the light-receiving part 16 formed by the gallium arsenide phosphide photodiode is more capable of reducing noise components arising from external light than the light-receiving part 16 formed by the silicon photodiode.

Sensitivity characteristics shown in FIG. 4B are those for an instance in which a gallium arsenide phosphide photodiode is used as the light-receiving part 16. In the example shown in FIG. 4B, the sensitivity is at a maximum for light having a wavelength of 565 nm, and the sensitivity for light having other wavelengths is normalized with respect thereto. The wavelength of light received by the light-receiving part 16 at which the sensitivity is at the maximum is within the range of wavelengths emitted by the light-emitting part 14 shown in FIG. 4A, but is not within a range of 700 nm to 1100 nm, which is known as the biological window (i.e., a wavelength region within which biological substances readily transmit light). In the example shown in FIG. 4B, the sensitivity of infrared light falling within the range of 700 nm to 1100 nm is set at a relative sensitivity of 0.3 (i.e., 30%) or less. The wavelength of light received by the light-receiving part 16 at which the wavelength is at the maximum (e.g. 565 nm) is preferably closer to the wavelength at which the intensity of light emitted by the light-emitting part 14 is at the maximum (i.e., 520 nm) than a lower limit of the biological window (i.e., 700 nm).

Figure 5:
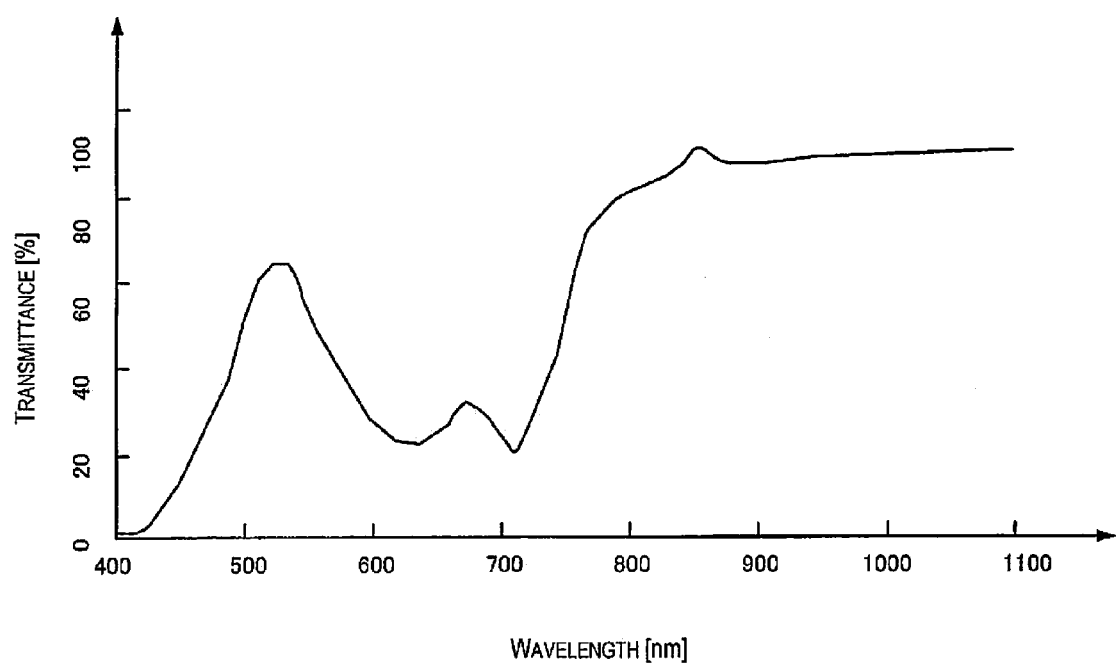
FIG. 5 is a drawing representing an example of light transmission characteristics of the substrate having the light-transmitting film.

FIG. 5 is a drawing representing an example of light transmission characteristics of the substrate coated with the light-transmitting film. Light transmission characteristics shown in FIG. 5 were obtained by calculating the transmittance using intensity of light before passing through the substrate 11 and intensity of light after passing through the substrate 11.

In the example shown in FIG. 5, in a range of wavelength equal to or less than 700 nm, which is the lower limit of the optical window in biological tissue, the transmittance is at a maximum for light having a wavelength of 525 nm. Also, in the range of wavelength equal to or less than 700 nm, which is the lower limit of the opticalwindow in biological tissue, the wavelength of maximum transmittance of light passing through at least one of the light transmission film 11-1 and the light-transmitting film 11-2 falls within a range of ±10% of the wavelength of the maximum intensity of light generated by the light-emitting part 14 shown, e.g., in FIG. 4A. It is preferable for the light transmission film 11-1 (11-2) to selectively transmit light emitted by the light-emitting part 14 (e.g., the valid reflected light R1' produced by the light R1 being reflected at the blood vessel BV, shown in FIG. 1A).

Figure 6A:
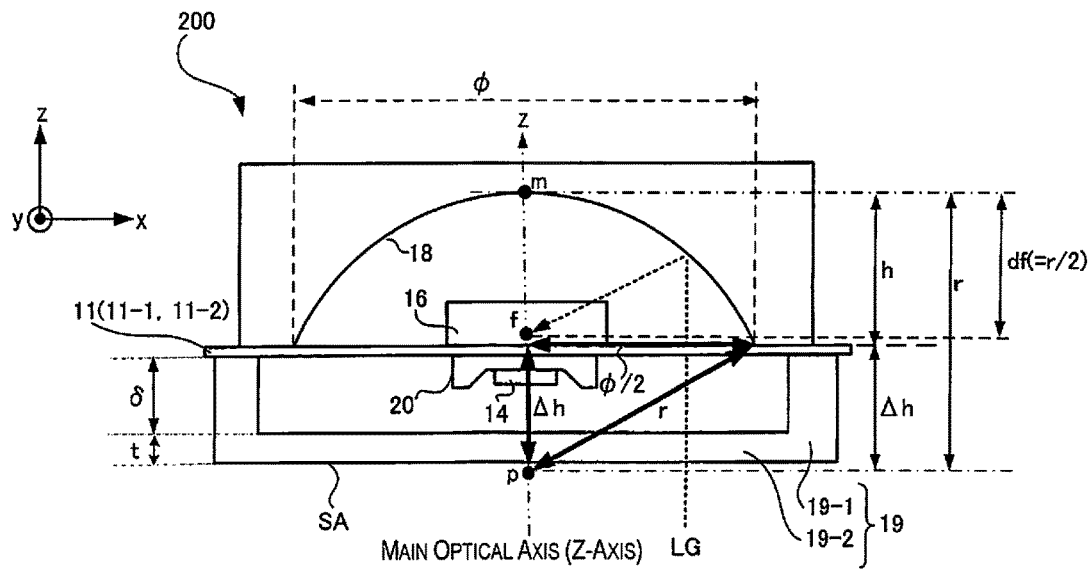
FIG. 6A is a drawing representing parameters relating to designing the reflecting part having the reflecting surface that uses a part of a spherical surface, and to an example of a method for designing the reflecting part.
Figure 6B:
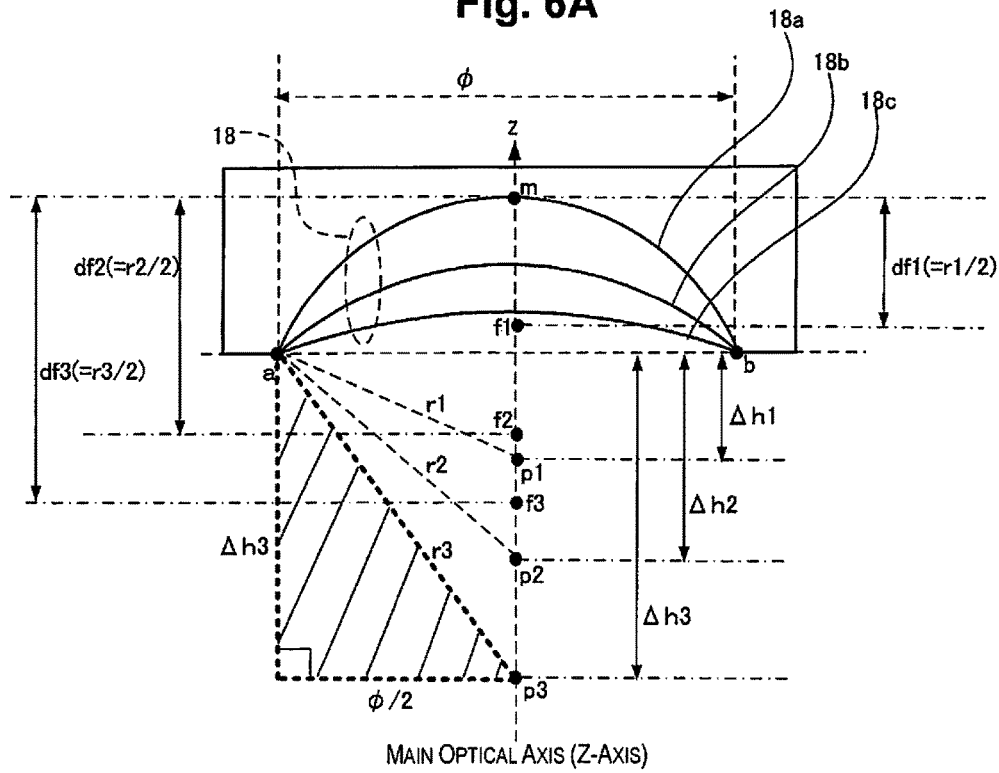
FIG. 6B is a drawing representing parameters relating to designing the reflecting part having the reflecting surface that uses the part of the spherical surface, and to an example of the method for designing the reflecting part.

Design of a Reflecting Part Having a Reflecting Surface that Uses a Part of a Spherical Surface Next, a design of the reflecting part having the reflecting surface that uses a part of a spherical surface will be described with reference to FIGS. 6 through 16. FIGS. 6A and 6B are drawings representing parameters relating to designing the reflecting part having the reflecting surface that uses a part of a spherical surface, and to an example of a method for designing the reflecting part.

In the example shown in FIG. 6A, a mutually perpendicular x-axis, y-axis, and z-axis are shown in order to define a three-dimensional space. The z-axis is defined as an optical axis (i.e., a main optical axis). A point of intersection between the z-axis and the reflecting surface of the reflecting part 18 is defined as an origin (i.e., a surface origin) m.

The aperture diameter of the reflecting surface of the reflecting part 18 is represented by cp. The reflecting surface of the reflecting part 18 includes a part of a spherical surface, which is a quadric surface. In the example shown in FIG. 6A, the reflecting surface includes a substantially hemispherical surface, which is a part of a spherical surface.

A focal point of the reflecting part 18 (i.e., a focal point of a light-collecting mirror including the reflecting surface) is f. When a light beam LG that is parallel to the optical axis (i.e., the z-axis) is incident on the reflecting part 18, the light is reflected on the reflecting part 18 and collects at the focal point f. The distance between the origin m and the focal point f is the focal distance df.

A distance that is twice that of the focal distance df is equivalent to the curvature radius r of the reflecting surface. Specifically, the focal distance df is equal to r/2. Also, in FIG. 6A, point p represents a center point of a spherical surface forming the reflecting surface of the reflecting part 18.

The height of the reflecting surface of the reflecting part 18 is represented by h. The height h is established by a distance from the second surface (i.e., the surface on the side towards the reflecting part 18) of the substrate 11 to the origin (i.e., the surface origin) m. Specifically, the height h of the reflecting surface represents the distance between a point m of intersection between the optical axis (i.e., the z-axis) and the reflecting surface (i.e., the surface origin m) and the second surface of the substrate 11 (i.e., the main surface of the substrate 11 that is arranged on a side towards the reflecting surface; the front surface of the substrate 11). The height h of the reflecting surface is unambiguously established in correspondence with the curvature radius r and the aperture diameter φ of the reflecting surface. Also, Δh is used to represent the difference between the height h of the reflecting surface and the curvature radius r of the reflecting surface. The difference Δh (may be referred to simply as Ah) is established by a distance from the second surface of the substrate 11 to the center point p of the spherical surface forming the reflecting surface.

Also, as described above, the height of the spacer member 19-1 in the protecting part 19 (i.e., a spacing between the substrate 11 and a surface of the contact member 19-2 that is opposite the contact surface SA) is represented by δ, and the thickness of the contact member 19-2 is represented by t.

A simulation will now be made for an instance in which each of the aperture diameter φ of the reflecting part 18, the height δ of the spacer member 19-1 (i.e., the spacing between the substrate 11 and the surface of the contact member 19-2 that is opposite the contact surface SA), and the thickness t of the contact member 19-2 is fixed to a predetermined value, and Δh or the focal distance df of the reflecting part 18 is varied. FIG. 6B is a drawing representing how the curvature radius r of the reflecting surface (i.e., the spherical surface forming the reflecting surface) and the shape of the reflecting surface of the reflecting part 18 vary in such an instance.

In FIG. 6B, Δh (i.e., the difference between the height h of the reflecting surface and the curvature radius r of the reflecting surface) is set to Δh1, Δh2, and Δh3. Correspondingly, the curvature radius r of the reflecting surface changes from r1 to r2 and r3. Specifically, the curvature radius is r1 at Δh1, the curvature radius is r2 at Δh2, and the curvature radius is r3 at Δh3.

Since the focal distance df of the reflecting part 18 (i.e., a reflecting light-collecting mirror) is half the curvature radius r, when curvature radius r changes, the focal distance df changes in correspondence with the curvature radius r. When the curvature radius is r1, the focal distance is represented by df1, and the focal point f of the reflecting part 18 is represented by f1. When the curvature radius is r2, the focal distance is represented by df2, and the focal point f of the reflecting part 18 is represented by f2. When the curvature radius is r3, the focal distance is represented by df3, and the focal point f of the reflecting part 18 is represented by f3.

In FIG. 6(B), when the curvature radius r changes, the shape of the reflecting surface including a spherical surface also changes in correspondence with the change in curvature radius r. Specifically, since φ is constant, the position of each of points a and b defining the aperture diameter is fixed; therefore, when the curvature radius r changes, the height h of the reflecting surface including a spherical surface also changes in accordance with the change in the curvature radius r. In FIG. 6B, the shape of the reflecting surface when the curvature radius r is equal to r1 is represented by 18a. The shape of the reflecting surface when the curvature radius r is equal to r2 is represented by 18b. The shape of the reflecting surface when the curvature radius r is equal to r3 is represented by 18c. Thus changing Δh makes it possible to change the three-dimensional shape and the height of the reflecting surface.

Although according to the above description, the three-dimensional shape and height of the reflecting surface are changed by changing the Δh, the shape of the reflecting surface can also be changed by changing the focal distance df. Specifically, when the φ of the reflecting surface is a fixed value (i.e., already known), changing, e.g., the focal distance df of the reflecting part 18 (i.e., the reflective optical system) changes the curvature radius r of (the spherical surface forming) the reflecting surface. When the curvature radius r changes, the difference Δh between the height h and the curvature radius r of the reflecting surface changes. The focal distance df of the reflecting surface and the difference Δh between the height h and the curvature radius r of the reflecting surface have a one-to-one correspondence relationship. When the focal distance df increases, Δh also increases. When the focal distance df of the reflecting part 18 is established, Δh is established.

The curvature radius r of the contact surface forming the reflecting surface (i.e., the curvature radius of the reflecting surface) can be represented using the following Equation 1 (refer to right-angled triangle indicated by thick arrows in FIG. 6A).

Mathematical formula 1

$$r=\sqrt{\{\Delta h^2+(\phi/2)^2\}} \quad (1)$$

Focusing, e.g., on a right-angled triangle shown at the lower left side of FIG. 6B shaded with diagonal lines, it can be seen, using the Pythagorean theorem, that the curvature radius r3 can be represented by the following Equation 2.

Mathematical formula 2

$$r3=\sqrt{\{\Delta h3^2+(\phi/2)^2\}} \quad (2)$$

Therefore, when a preferred focal distance of the reflecting surface is established, the curvature radius r can be unambiguously established using the above Equation 1, and the spherical surface forming the reflecting surface is established. Also, since the aperture diameter φ of the reflecting surface (i.e., the diameter of the outer circumferential circle of the reflecting surface with respect to the plan view) is fixed (i.e., already known), the height h of the reflecting surface is unambiguously established. Specifically, when φ is established, a slicing position of the spherical surface (i.e., a position at which the spherical surface is sliced along an x-y plane) is correspondingly established, whereby the three-dimensional shape and height of the reflecting surface are unambiguously established.

The above-described method for designing a reflective optical system can be used to design the reflecting part 18 so as to reduce the once-reflected light and the twice-reflected light (which are both invalid directly reflected light) shown in FIG. 1B.

Figure 7:
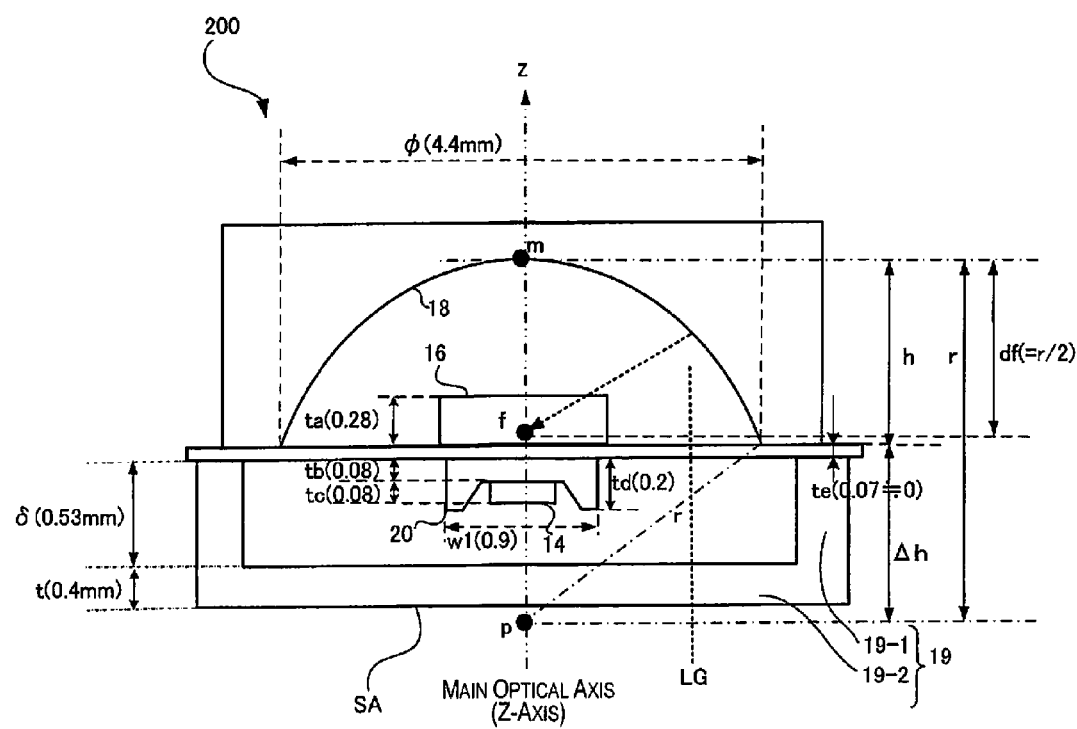
FIG. 7 is a drawing representing an example of dimensions of main configurations in the biological information detector.

A Simulation of Behavior of Reflected Light in an Instance in which Focal Distance Df or Difference Δh is Changed A description will now be given for, e.g., a result of a simulation of a behavior of reflected light in an instance in which the focal distance df or the difference Δh is changed, with reference to FIGS. 7 through 16. FIG. 7 is a drawing representing an example of dimensions of main configurations in the biological information detector (the dimensions are not limited to those described in the example below). As shown in FIG. 7, the aperture diameter φ is set to 4.4 mm, the height δ of the spacer member 19-1 of the protecting part 19 (or, the spacing) is set to 0.53 mm, the thickness t of the contact member 19-2 (i.e., the thickness of the glass) is set to 0.4 mm.

As shown in FIG. 7, the thickness to of the light-receiving part 16 is, e.g., 0.28 mm, the thickness tb of a bottom part of the reflector 20 is, e.g., 0.08 mm, the thickness tc of the light-emitting part 14 is, e.g., 0.08 mm, and the maximum height td of the reflector 20 is, e.g., 0.2 mm.

The actual thickness te of the substrate 11 (including the light-transmitting film, i.e., the light-transmitting resist films 11-1 and 11-2) is, e.g., about 0.07 mm. However, since the substrate 11 is sufficiently thin, and, as described above, the light-transmitting resist film maintains smoothness and reduces the difference in refractive index in relation to air, the thickness te of the substrate 11 is ignored in the simulation of the behavior of the reflected light (i.e., te is considered zero). Also, the reflecting surface of the reflecting part 18 includes a part of a spherical surface, which is a quadric surface, as described above.

The refractive index of glass forming the protecting part 19 is, e.g., 1.52. The refractive index of polyamide forming the substrate 11 is, e.g., 1.7. Polyarylate (with a refractive index of 1.61) may also be used as a material for the transparent substrate.

The behavior of directly reflected light (i.e., invalid light or invalid reflected light) and the behavior of light having biological information (i.e., valid light or valid reflected light) in an instance in which the focal distance df of the reflecting surface (i.e., a spherical mirror) (or, the difference Δh between the height of the reflecting surface and the curvature radius of the reflecting surface) is changed (with other parameters being fixed) will now be discussed in relation to the biological information detector 200 shown in FIG. 7.

FIGS. 8A and 8B are drawings used to describe a behavior of directly reflected light (i.e., invalid light) in an instance in which df=1.18 mm (Δh=0.4 m). As shown in FIG. 8B, the reflecting surface of the reflecting part 18 is a substantially hemispherical surface. In FIG. 8A, the reflecting surface 18-1 of the reflecting part 18 and the spacer member 19-1 are shown, not as a cross-section, but as a shape having spatial depth (this also applies to subsequent drawings).

In FIG. 8A, trajectories of directly reflected light (i.e., invalid light), produced by light emitted by the light-emitting part 14 (not including light reflected on the reflector or another member) reflecting on a side of the contact member 19-2 of the protecting part 19 towards the contact surface SA (i.e., the contact surface SA or a vicinity thereof) are shown by solid arrows.

As can be seen from FIG. 8A, there is a high probability of once-reflected light, which is light emitted by the light-emitting part 14 reflecting once on the side of the contact member 19-2 towards the contact surface SA, being incident on the light-receiving region (i.e., the light-receiving surface) 16-1 of the light-receiving part 16. Specifically, there is a tendency towards a higher ratio of the amount of once-reflected incident light (i.e., incident light resulting from the once-reflected light being reflected by the reflecting surface and being incident on the light-receiving part 16) in relation to the total amount of light received at the light-receiving part 16.

For example, once-reflected light A1 reflects once at a point N1 on the contact member 19-2 on the side towards the contact surface SA. The once-reflected light passes through the substrate 11, reflects on the reflecting part 18, and reaches the light-receiving region 16-1 of the light-receiving part 16 in a direct manner (i.e., without undergoing complex reflections or scattering). Once-reflected light A2 reflects once at a point N2 on the contact member 19-2 on the side towards the contact surface SA. The once-reflected light passes through the substrate 11, reflects on the reflecting part 18, and reaches (i.e., is incident on) the light-receiving region 16-1 of the light-receiving part 16 in a direct manner. Also, once-reflected light A3 reflects once at a point N3 on the contact member 19-2 on the side towards the contact surface SA. The once-reflected light passes through the substrate 11, reflects on the reflecting part 18, and reaches (i.e., is incident on) the light-receiving region 16-1 of the light-receiving part 16 in a direct manner.

Meanwhile, as described above using FIG. 1A, reflected light R1' reflected at the blood vessel BV (i.e., valid reflected light having biological information) is incident on the light-receiving region (i.e., the light-receiving surface) 16-1 of the light-receiving part 16.

Figure 9:
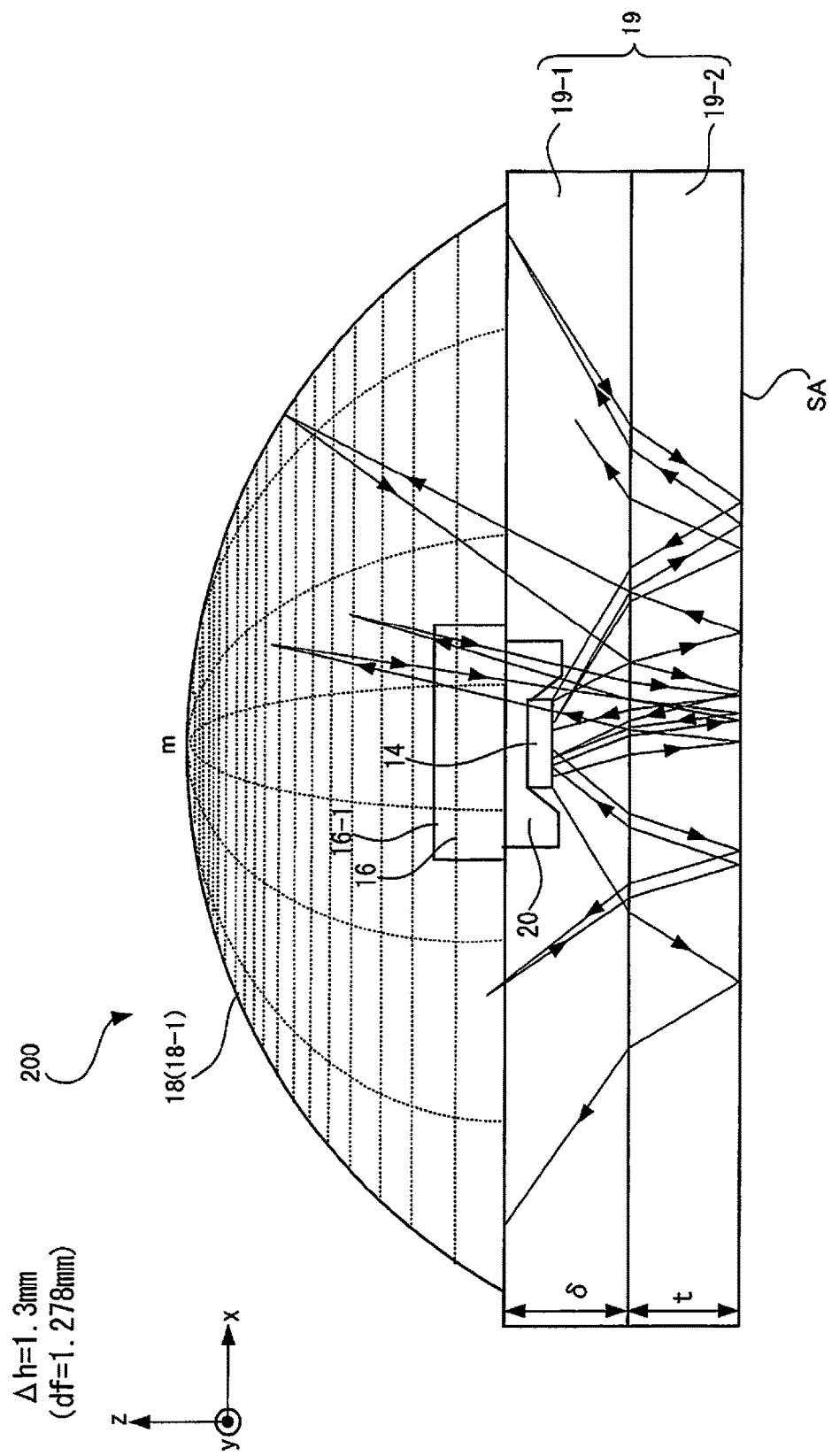
FIG. 9 is a drawing used to describe a behavior of directly reflected light in an instance in which df=1.278 mm (Δh=1.3 m)

Next, a description will be made with reference to FIG. 9. FIG. 9 is a drawing used to describe a behavior of directly reflected light in an instance in which df=1.278 mm (Δh=1.3 m). Trajectories of directly reflected light (i.e., invalid light), produced by light emitted by the light-emitting part 14 reflecting on a side of the contact member 19-2 of the protecting part 19 towards the contact surface SA (i.e., the contact surface SA or a vicinity thereof) in the example shown in FIG. 9 are shown by solid arrows.

As can be seen in FIG. 9, there are substantially no instances of once-reflected light, which is the light emitted by the light-emitting part 14 reflecting once on the side of the contact member 19-2 towards the contact surface SA, being incident on the light-receiving region (i.e., the light-receiving surface) 16-1 of the light-receiving part 16. There are also substantially no instances of twice-reflected light, which is the light emitted by the light-emitting part 14 reflecting twice on the side of the contact member 19-2 towards the contact surface SA, being incident on the light-receiving region (i.e., the light-receiving surface) 16-1 of the light-receiving part 16.

Specifically, there is a tendency for the ratio of the amount of incident light resulting from the directly reflected light (including once-reflected light and twice-reflected light) being reflected by the reflecting surface and being incident on the light-receiving part 16 (i.e., directly reflected incident light) in relation to the total amount of light received at the light-receiving part 16 to be significantly minimized.

Meanwhile, as described above using FIG. 1A, reflected light R1' reflected at the blood vessel BV (i.e., valid reflected light having biological information) arrives at (i.e., is incident on) the light-receiving region (i.e., the light-receiving surface) 16-1 of the light-receiving part 16.

Figure 10:
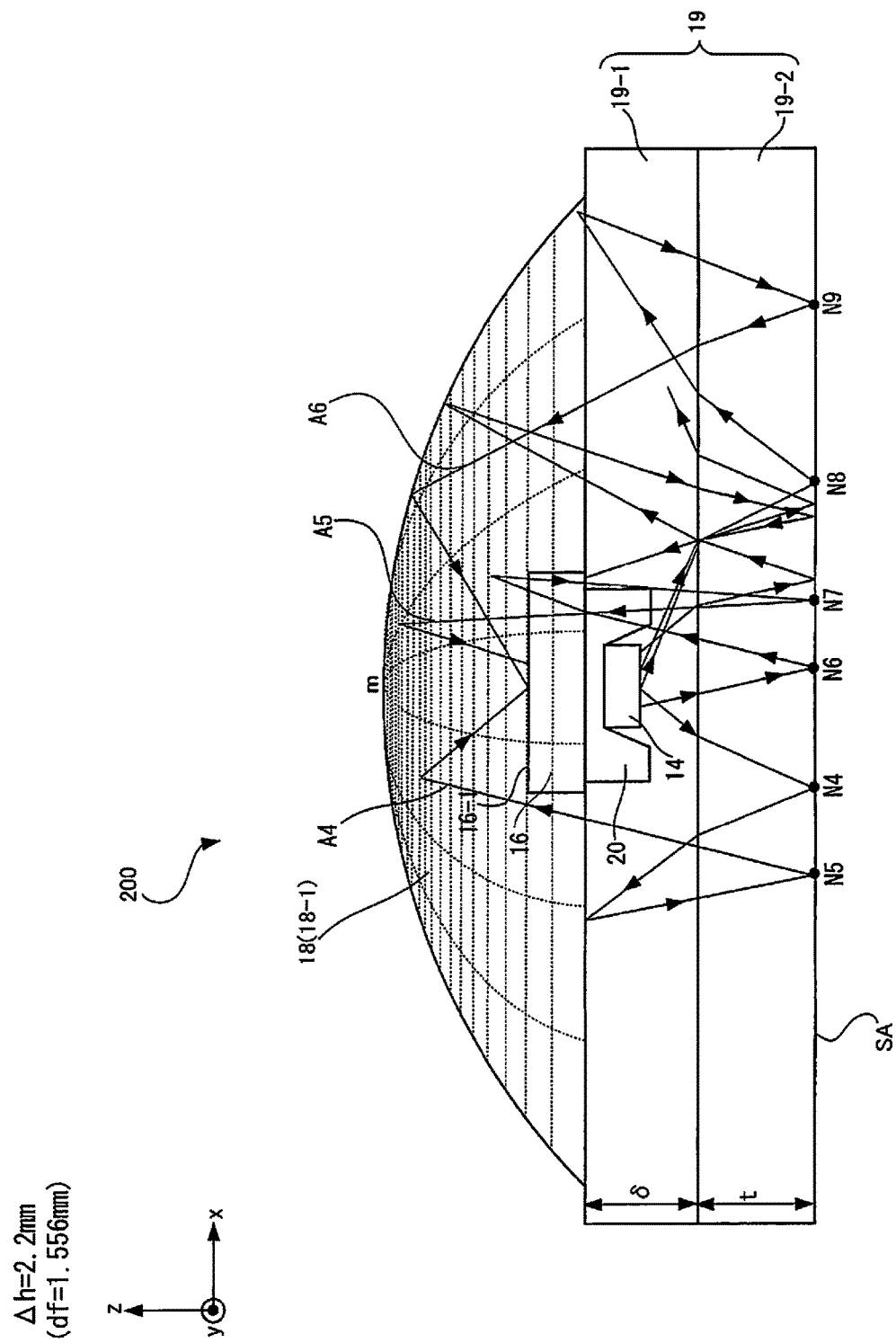
FIG. 10 is a drawing used to describe a behavior of directly reflected light in an instance in which df=1.556 mm (Δh=2.2 m)

Next, a description will be made with reference to FIG. 10. FIG. 10 is a drawing used to describe a behavior of directly reflected light in an instance in which df=1.556 mm (Δh=2.2 m). Trajectories of directly reflected light (i.e., invalid light), produced by light emitted by the light-emitting part 14 reflecting on a side of the contact member 19-2 of the protecting part 19 towards the contact surface SA (i.e., the contact surface SA or a vicinity thereof) in the example shown in FIG. 10 are shown by solid arrows.

As can be seen in FIG. 10, there is a high probability of the twice-reflected light, which is the light emitted by the light-emitting part 14 reflecting twice on the side of the contact member 19-2 towards the contact surface SA, being incident on the light-receiving region (i.e., the light-receiving surface) 16-1 of the light-receiving part 16.

Specifically, there is a tendency towards a higher ratio of the amount of incident light resulting from the twice-reflected light, which is a directly reflected light (i.e., invalid light), being reflected by the reflecting surface and being incident on the light-receiving part 16 (i.e., twice-reflected incident light) in relation to the total amount of light received at the light-receiving part 16.

For example, twice-reflected light A4 is reflected twice, at points N4 and N5 on the contact member 19-2 on the side towards the contact surface SA. The twice-reflected light passes through the substrate 11, reflects on the reflecting part 18, and reaches (i.e., is incident on) the light-receiving region 16-1 of the light-receiving part 16 in a direct manner. Also, twice-reflected light A5 reflects twice at points N6 and N7 on the contact member 19-2 on the side towards the contact surface SA. The twice-reflected light passes through the substrate 11, reflects on the reflecting part 18, and reaches (i.e., is incident on) the light-receiving region 16-1 of the light-receiving part 16 in a direct manner. Also, twice-reflected light A6 reflects twice at points N8 and N9 on the contact member 19-2 on the side towards the contact surface SA. The twice-reflected light passes through the substrate 11, reflects on the reflecting part 18, and reaches (i.e., is incident on) the light-receiving region 16-1 of the light-receiving part 16 in a direct manner.

Meanwhile, as described above using FIG. 1A, reflected light R1' reflected at the blood vessel BV (i.e., valid reflected light having biological information) arrives at (i.e., is incident on) the light-receiving region (i.e., the light-receiving surface) 16-1 of the light-receiving part 16.

Figure 11:
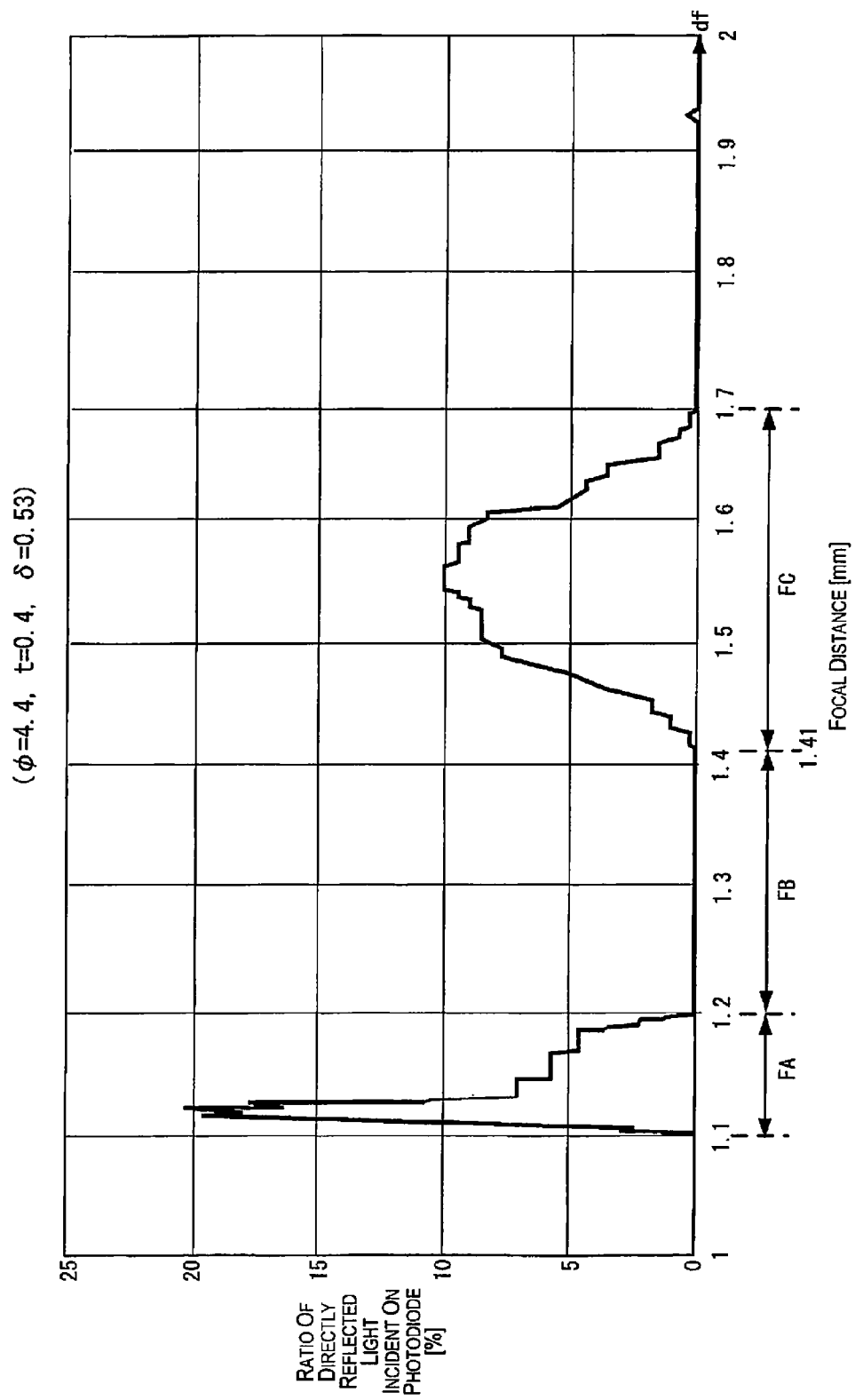
FIG. 11 is a drawing representing a change in a ratio (%) of the amount of directly reflected light incident on the light-receiving part (photodiode) in an instance in which the focal distance df is gradually increased where the aperture diameter φ=4.4 mm, t=0.4 mm, and δ=0.53 mm.

A simulation of a behavior of the directly reflected light was repeatedly performed, and a correlation between changes in the focal distance of the reflecting surface and the ratio of directly reflected light (i.e., invalid light) incident on the light-receiving part was studied. A result is shown in FIG. 11. FIG. 11 is a drawing representing a change in a ratio (%) of the amount of directly reflected light incident on the light-receiving part (photodiode) in relation to the total amount of light received at the light-receiving part 16 in an instance in which the focal distance df is gradually increased where the aperture diameter $\phi=4.4$ mm, $t=0.4$ mm, and $\delta=0.53$ mm.

In FIG. 11, gradually increasing the focal distance df of the reflecting surface results first in a focal distance range FA (i.e., a range of focal distance df from 1.1 to 1.2) in which a ratio, with respect to an amount of light received at the light-receiving region 16-1 of the light-receiving part 16, of light beams that reflect once at the contact member 19-2 of the protecting part 19 on a side towards the contact surface SA, then reflect again at the reflecting surface, and arrive at the light-receiving region of the light-receiving part in a direct manner, is higher than a predetermined first threshold value (approximately equal to 0%). The focal distance range FA is defined as a first focal distance range. The first focal distance range is a focal distance range that corresponds to single reflections.

Further increasing the focal distance df of the reflecting surface results next in a focal distance range FB (i.e., a range of focal distance df from 1.2 to 1.41) in which almost no once-reflected light reaches the light-receiving region of the light-receiving part 16. The focal distance range FB is defined as a second focal distance range. The second focal distance range is a focal distance range within which incidence of directly reflected light on the light-receiving part 16 is minimized.

Further increasing the focal distance df of the reflecting surface results next in a focal distance range FC (i.e., a range of focal distance df from 1.41 to 1.7) in which a ratio, with respect to an amount of light received at the light-receiving region of the light-receiving part 16, of light beams that reflect twice at the contact member 19-2 of the protecting part 19 on a side towards the contact surface SA, then reflects again at the reflecting surface, and arrives at the light-receiving region 16-1 of the light-receiving part 16 in a direct manner, is higher than a predetermined second threshold value (approximately equal to 0%). The focal distance range FC is defined as a third focal distance range. The third focal distance range is a focal distance range that corresponds to double reflections.

Next, a description will be given for a behavior of reflected light including, in addition to invalid light, valid light having biological information (i.e., valid reflected light; light R1' shown in FIG. 1A. The behavior of reflected light including invalid light and valid light is revealed by examining the change in the S/N of a biological information detection signal (e.g., pulse information detection signal) outputted from the light-receiving part 16. The behavioral tendency of invalid light (i.e., invalid reflected light) has been revealed in FIG. 11.

Therefore, a tendency with which the S/N of the detection signal outputted from the light-receiving part 16 changes can be compared with the behavioral tendency of invalid light (i.e., invalid reflected light) shown in FIG. 11 to identify a behavioral tendency of valid light (i.e., valid reflected light) having biological information. For example, if there appears a focal distance range with an increasing S/N in the detection signal within a focal distance range in which the amount of invalid light (i.e., noise N) reaching the light-receiving region 16-1 of the light-receiving part 16 is significantly minimized indicates that the amount of valid light (i.e., signal S) is increasing in the focal distance range.

Figure 12:
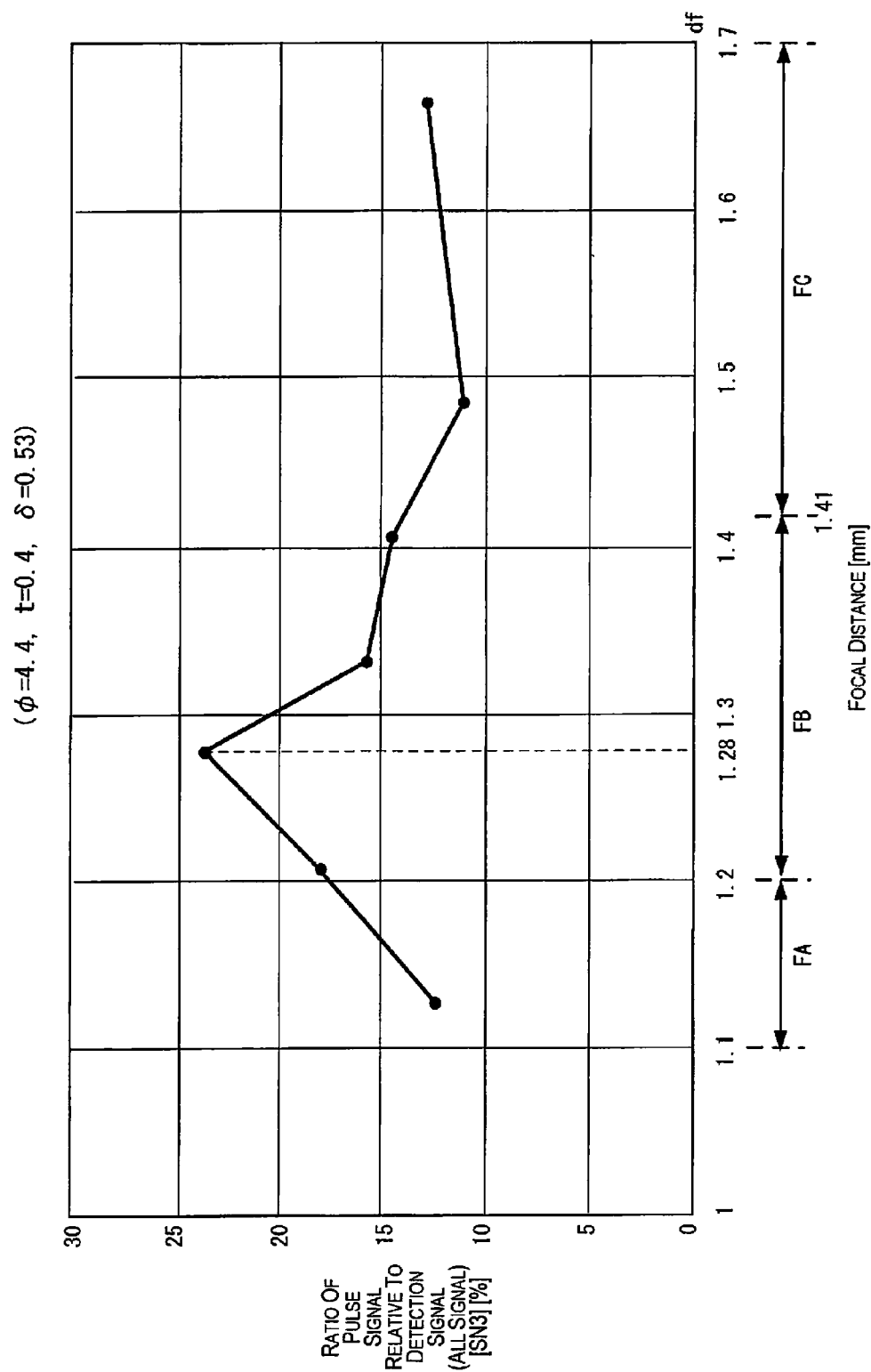
FIG. 12 is a drawing representing a change in a ratio (S/N) of valid light having pulse rate information incident on the light-receiving part (photodiode) in an instance in which the focal distance df is gradually increased where the aperture diameter φ=4.4 mm, t=0.4 mm, and δ=0.53 mm.

FIG. 12 is a drawing representing an example of a change in a ratio of a pulse signal (%) relative to a pulse information detection signal (i.e., all signal including pulse signal having pulse information as well as noise) in an instance in which the focal distance df is gradually increased where the aperture diameter $\phi=4.4$ mm, $t=0.4$ mm, and $\delta=0.53$ mm.

As can be seen in FIG. 12, the S/N of the detection signal peaks at a vicinity of a focal distance df of 1.28. The focal distance df corresponding to the peak (i.e., df=1.28) is within the second focal distance range FB (i.e., a range of focal distance df from 1.2 to 1.41) shown in FIG. 11.

Also, it can be seen that the S/N of the detection signal in each of the first focal distance range FA (i.e., a range of focal distance df from 1.1 to 1.2) and the third focal distance range FC (i.e., a range of focal distance df from 1.41 to 1.7) shown in FIG. 11 is generally lower than the S/N of the detection signal in the second focal distance range FB (i.e., a range of focal distance df from 1.2 to 1.41).

As described above, the second focal distance range FB is a focal distance range in which directly reflected light (i.e., invalid light) is significantly minimized. Therefore, the fact that the S/N of the detection signal in the second focal distance range FB is higher than in other focal distance ranges (i.e., FA and FC) indicates that, specifically, the ratio of valid light (i.e., valid reflected light) in the second focal distance range FB is higher (i.e., more valid light is incident on the light-receiving region 16-1 of the light-receiving part 16) than in the other focal distance ranges (i.e., the first focal distance range FA and the third focal distance range FC).

Specifically, in the second focal distance range FB (i.e., a range of focal distance df from 1.2 to 1.41), in addition to the effect of minimizing the incidence of directly reflected light (i.e., invalid light) on the light-receiving region 16-1 of the light-receiving part 16, an effect of increasing the amount of valid light (i.e., valid reflected light; light R1' in FIG. 1A) having pulse rate information as biological information can be obtained. Therefore, setting the focal distance df of the reflecting surface 18-1 of the reflecting part 18 within the focal distance range FB makes it possible to increase the S/N of the detection signal corresponding to detection of the pulse rate as biological information. Specifically, improving the S/N of the detection signal makes it possible to perform detection with a higher degree of accuracy. In particular, setting the focal distance df of the reflecting surface 18-1 of the reflecting part 18 at a focal distance corresponding to a vicinity of the peak value of the S/N of the detection signal makes it possible to maximize the detection accuracy.

Although in the example described above, optical characteristics of the reflecting part were analyzed using the focal distance df as a parameter, a similar result can be obtained in an instance in which $\Delta h$ is used as a parameter.

Figure 13:
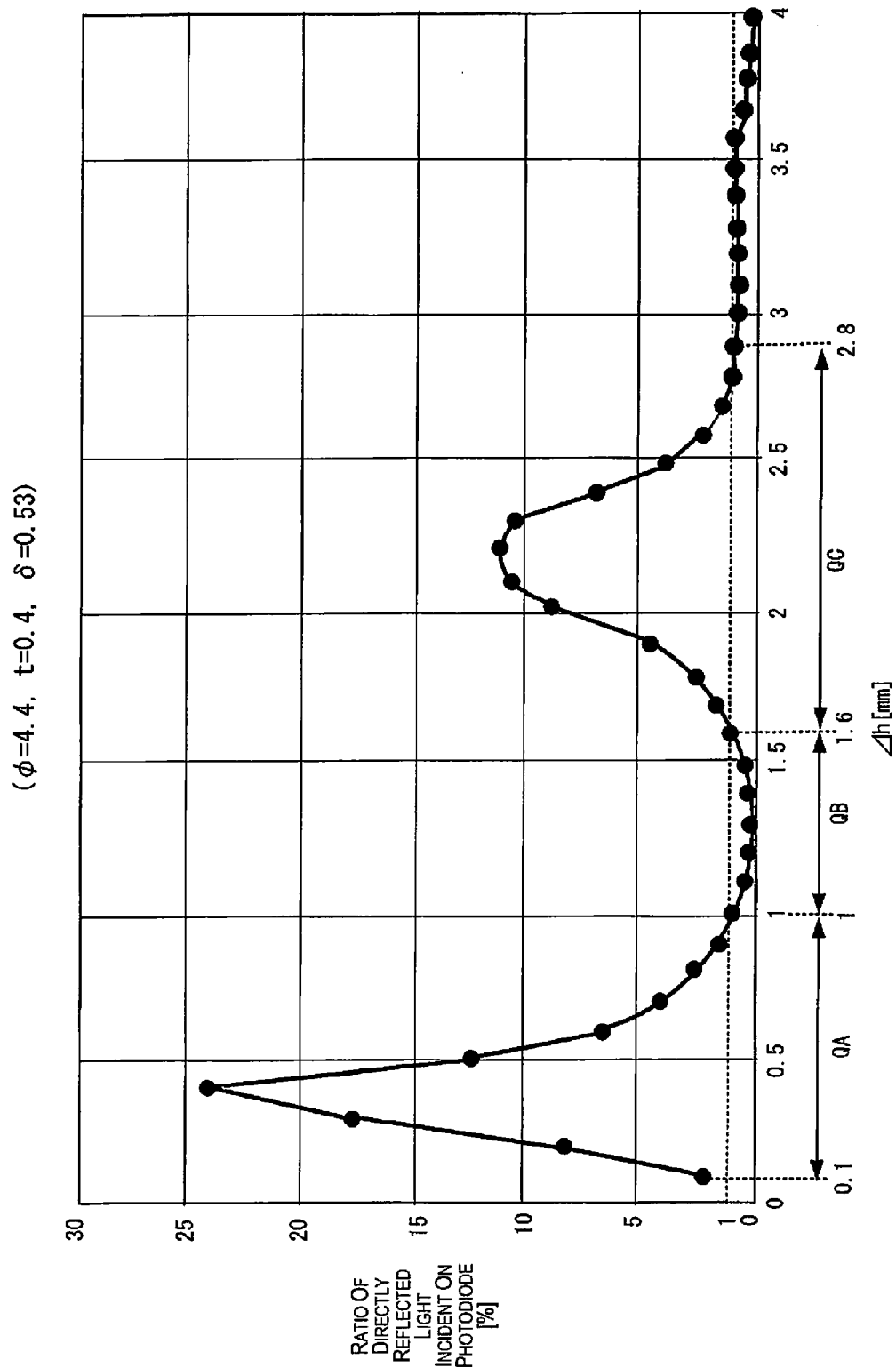
FIG. 13 is a drawing representing a change in the ratio (%) of the amount of directly reflected light incident on the light-receiving part (photodiode) in an instance in which Δh is gradually increased where the aperture diameter φ=4.4 mm, t=0.4 mm, and δ=0.53 mm.

FIG. 13 is a drawing representing a change in the ratio (%) of the amount of directly reflected light (i.e., invalid light) incident on the light-receiving part (photodiode) in an instance in which Δh is gradually increased where the aperture diameter φ=4.4 mm, t=0.4 mm, and δ=0.53 mm. As described above, there is a one-to-one correspondence relationship between the focal distance df and the difference Δh between the height h and the curvature radius r of the reflecting surface; when one increases, the other also increases. In the example shown in FIG. 13, the change in the ratio (%) of the amount of directly reflected light is examined using Δh as a parameter (i.e., a variable).

In FIG. 13, there exist a Δh range QA corresponding to single reflections (i.e., Δh is within a range of 0.1 to 1.0, in which the ratio is equal to or above 1%; first Δh range); a Δh range QB in which incidence of the directly reflected light on the light-receiving part is minimized (i.e., Δh is within a range of 1.0 to 1.6, in which the ratio is equal to or below 1%; second Δh range); and a Δh range QC corresponding to double reflections (Δh is within a range of from 1.6 to 2.8, in which the ratio is above 1%; third Δh range). In the example shown in FIG. 13, the predetermined first and second threshold values are both 1%.

Figure 14:
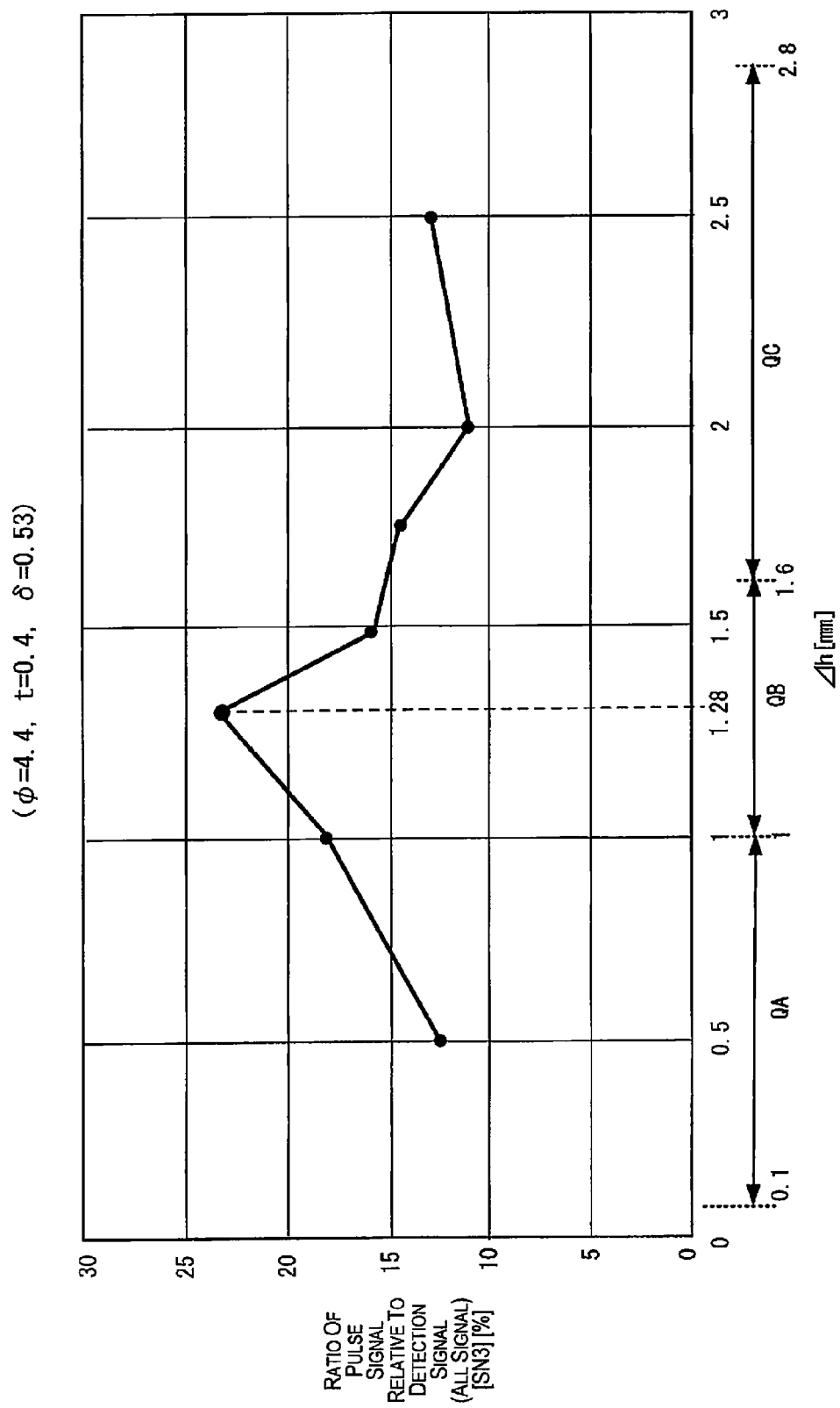
FIG. 14 is a drawing representing a change in the ratio (S/N) of valid light having pulse rate information incident on the light-receiving part (photodiode) in an instance in which Δh is gradually increased where the aperture diameter φ=4.4 mm, t=0.4 mm, and δ=0.53 mm.

FIG. 14 is a drawing representing another example of a change in the ratio of the pulse signal (%) relative to a pulse information detection signal (i.e., all signals including pulse signal having pulse information as well as noise) in an instance in which Δh is gradually increased where the aperture diameter φ=4.4 mm, t=0.4 mm, and δ=0.53 mm. As can be seen in FIG. 14, the S/N of the detection signal outputted from the light-receiving part 16 peaks at a vicinity of a Δh of 1.28. Δh corresponding to the peak (i.e., Δh=1.28) is within the Δh range QB shown in FIG. 13, in which incidence of directly reflected light on the light-receiving part is minimized (i.e., a range of Δh from 1.0 to 1.6; the second Δh range).

It can also be seen that the S/N of the detection signal in each of the th range QA corresponding to single reflections (i.e., a range of Δh from 0.1 to 1.0; the first Δh range) and the Δh range QC corresponding to double reflections (i.e., a range of Δh from 1.6 to 2.8; the third Δh range) shown in FIG. 13 is generally lower than the S/N of the detection signal in the second th range QB. Specifically, it can be seen that in the second Δh range QB (i.e., a range of Δh from 1.0 to 1.6), in addition to the effect of minimizing the incidence of directly reflected light on the light-receiving region 16-1 of the light-receiving part 16, an effect of increasing the incidence amount of valid light having pulse rate information can be obtained, whereby the S/N of the pulse rate information detection signal increases (i.e., the S/N of the detection signal improves) relative to other Δh regions (i.e., the first Δh range QA and the third Δh range QC).

Therefore, setting Δh within the second Δh range QB makes it possible to improve the S/N of the detection signal corresponding to detection of the pulse rate as biological information. Specifically, the S/N of the detection signal can be improved, thereby making it possible to perform detection with a higher degree of accuracy. In particular, setting Δh at a value corresponding to a vicinity of the peak value of the S/N of the detection signal makes it possible to maximize the detection accuracy.

Figure 15:
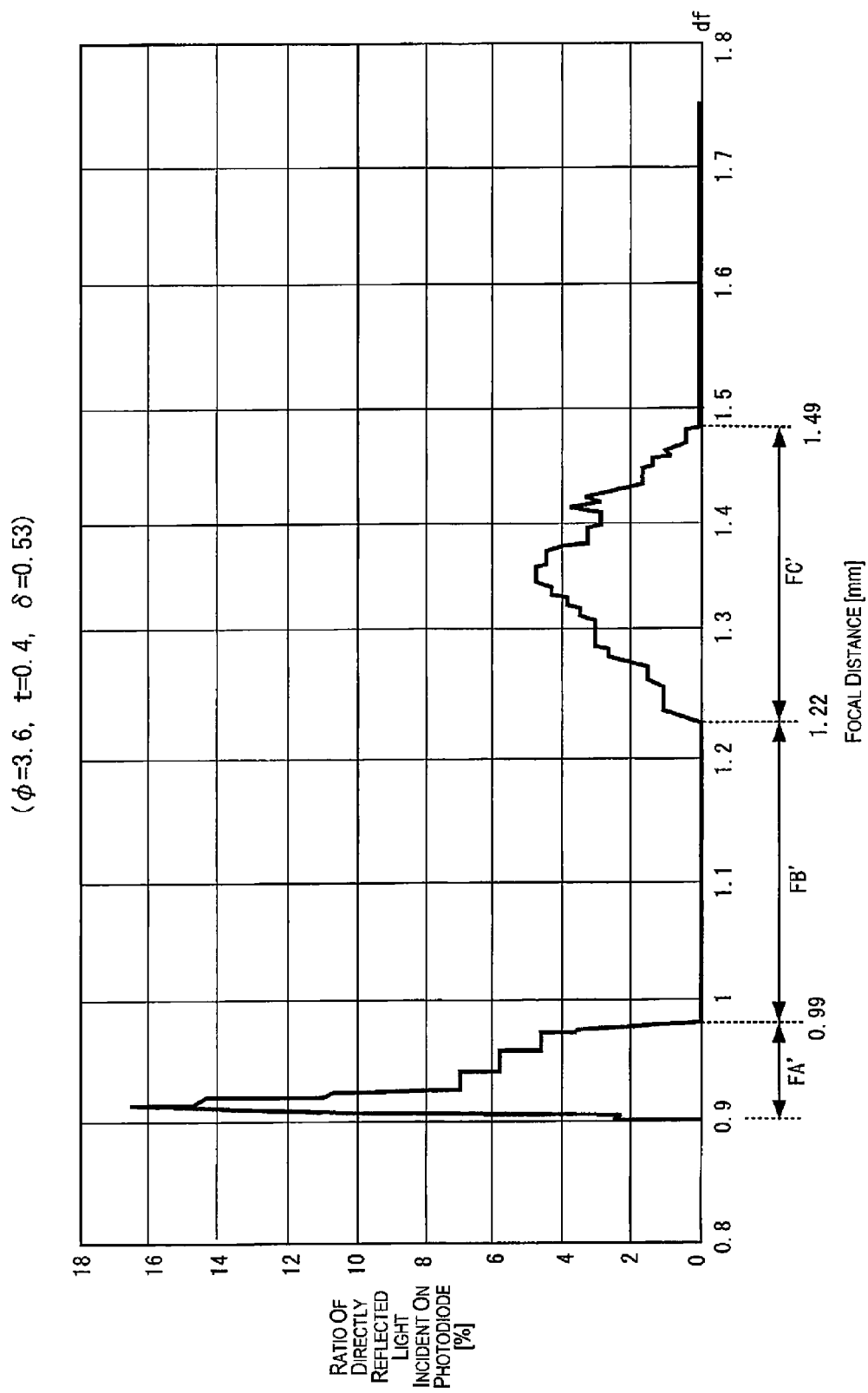
FIG. 15 is a drawing representing a change in the ratio (%) of the amount of directly reflected light incident on the light-receiving part (photodiode) in an instance in which the focal distance df is gradually increased where the aperture diameter φ=3.6 mm, t=0.4 mm, and δ=0.53 mm.
Figure 16:
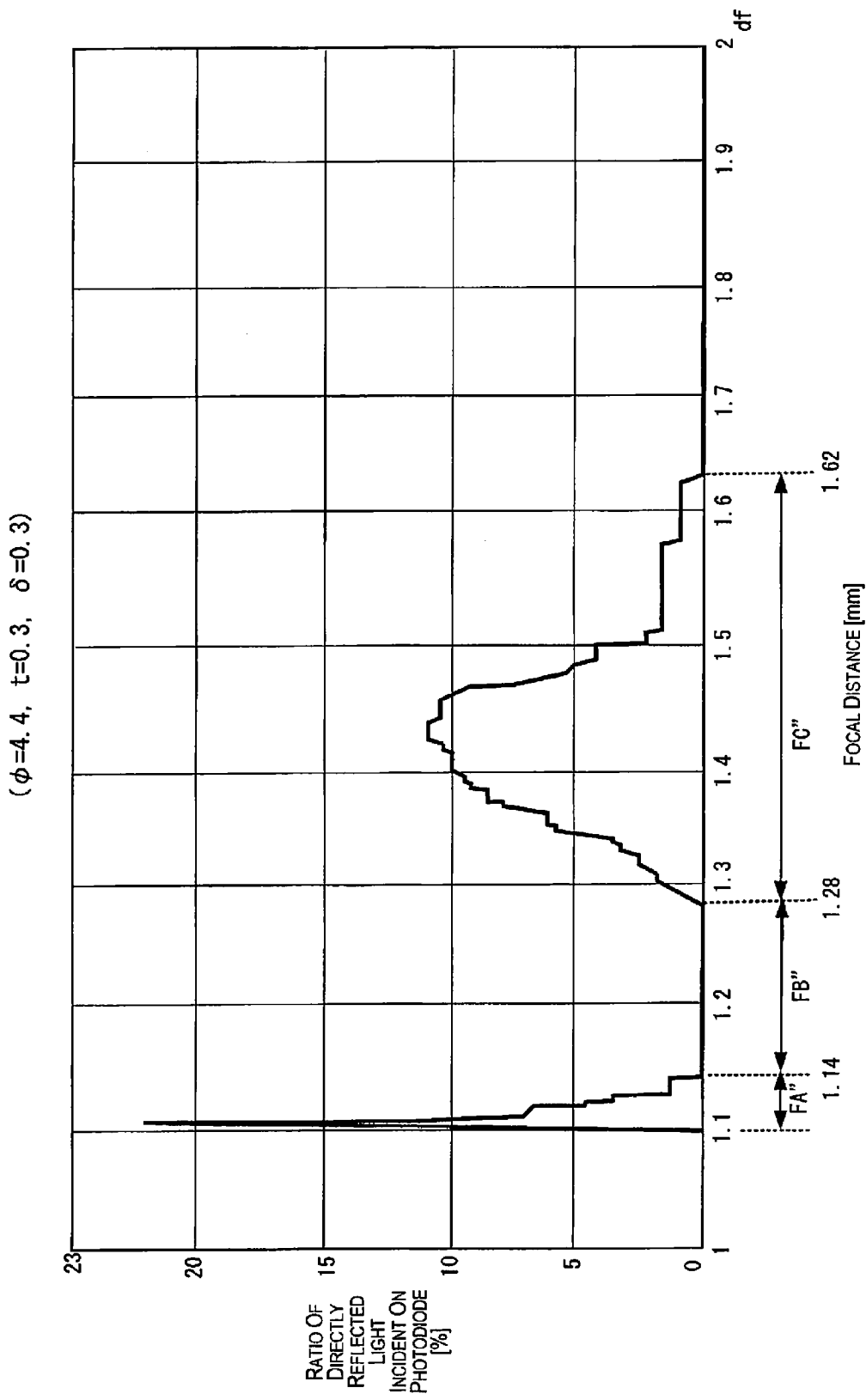
FIG. 16 is a drawing representing a change in the ratio (%) of the amount of directly reflected light incident on the light-receiving part (photodiode) in an instance in which the focal distance df is gradually increased where the aperture diameter φ=4.4 mm, t=0.3 mm, and δ=0.3 mm.

FIGS. 15 and 16 represent results obtained when dimension conditions that represent preconditions are partially changed and a similar simulation is performed.

Specifically, FIG. 15 is a drawing representing a change in the ratio (%) of the amount of directly reflected light incident on the light-receiving part (photodiode) in an instance in which the focal distance df is gradually increased where the aperture diameter φ=3.6 mm, t=0.4 mm, and δ=0.53 mm. In the example shown in FIG. 15, the aperture diameter φ has been changed from 4.4 mm (as in the example described above) to 3.6 mm.

In the example shown in FIG. 15, it can again be seen that a first focal distance range FA' (a range of focal distance df from 0.9 to 0.99), a second focal distance range FB' (a range of focal distance df from 0.99 to 1.22), and a third focal distance range FC' (a range of focal distance df from 1.22 to 1.49) are present.

FIG. 16 is a drawing representing a change in the ratio (%) of the amount of directly reflected light incident on the light-receiving part (photodiode) in an instance in which the focal distance df is gradually increased where the aperture diameter φ=4.4 mm, t=0.3 mm, and δ=0.3 mm. In the example shown in FIG. 16, the thickness t of the contact member 19-2 has been changed from 0.4 mm (as in the example described above) to 0.3 mm, and the height δ (i.e., the spacing) of the spacer member 19-1 has been changed from 0.53 (as in the example described above) to 0.3 mm.

In the example shown in FIG. 16, a first focal distance range FA" (a range of focal distance df from 1.1 to 1.14), a second focal distance range FB" (a range of focal distance df from 1.14 to 1.28), and a third focal distance range FC" (a range of focal distance df from 1.28 to 1.62) are again present.

In an instance in which any of the aperture diameter φ, the thickness t of the contact member 19-2, and the height δ (i.e., the spacing) of the spacer member 19-1 has been changed, the second focal distance range thus appears between the focal distance range and the third focal distance range. Therefore, it can be seen that a main parameter that has the largest effect on the behavior of directly reflected light of such description is focal distance df (or Δh). Therefore, using the focal distance df (or Δh) as a design parameter is effective when designing the reflecting part 18 to realize preferable reflective characteristics.

When such observations are taken into consideration, the focal distance df of the reflecting surface of the reflecting part 18 is preferably set within the second focal distance range FB (FB', FB"), which is between the first focal distance range FA (FA', FA") and the third focal distance range FC (FC', FC").

As described above, when the focal distance df of the reflecting surface is established, the curvature radius of the spherical surface forming the reflecting surface is established. The spherical surface is therefore unambiguously established. Also, since the aperture diameter of the reflecting surface is already known, the position at which the spherical surface is sliced along the x-y plane is unambiguously established, and height h of the reflecting surface including a part of the spherical surface is thereby established. The three-dimensional shape and height of the reflecting surface of the reflecting part 18 is thereby unambiguously established.

Using the design method described above to adjust the reflective characteristics of the reflecting part 18 makes it possible to minimize incidence of the once-reflected light (i.e., invalid light) and the twice-reflected light (i.e., invalid light) on the light-receiving region 16-1 of the light-receiving part 16 and increase the probability of valid reflected light, having biological information, being incident on the light-receiving region 16-1 of the light-receiving part 16. It is thereby possible to minimize adverse effects (e.g., a decrease in the S/N of the detection signal outputted from the light-receiving part 16) of light reflected on the contact member 19-2 on a side towards the contact surface SA (i.e., directly reflected light).

Second Embodiment

In the present embodiment, the reflecting surface of the reflecting part includes a part of a paraboloid, which is a quadric surface. Whereas in the previous embodiment, the reflecting surface of the reflecting part was constituted using a spherical surface, which is a quadric surface, the reflecting surface can also be constituted using a non-spherical surface (i.e., a paraboloid).

A paraboloid of revolution can be used as the paraboloid. The paraboloid of revolution is a quadric surface obtained by revolving a parabola, using a z-axis, which is an axis of symmetry, as an axis of revolution, where an z-axis, among mutually perpendicular x-, y-, and z-axes that define a 3-dimensional space, is an optical axis (i.e., a curved surface represented by a quadratic equation with three unknowns of x, y, and z).

Figure 17A:
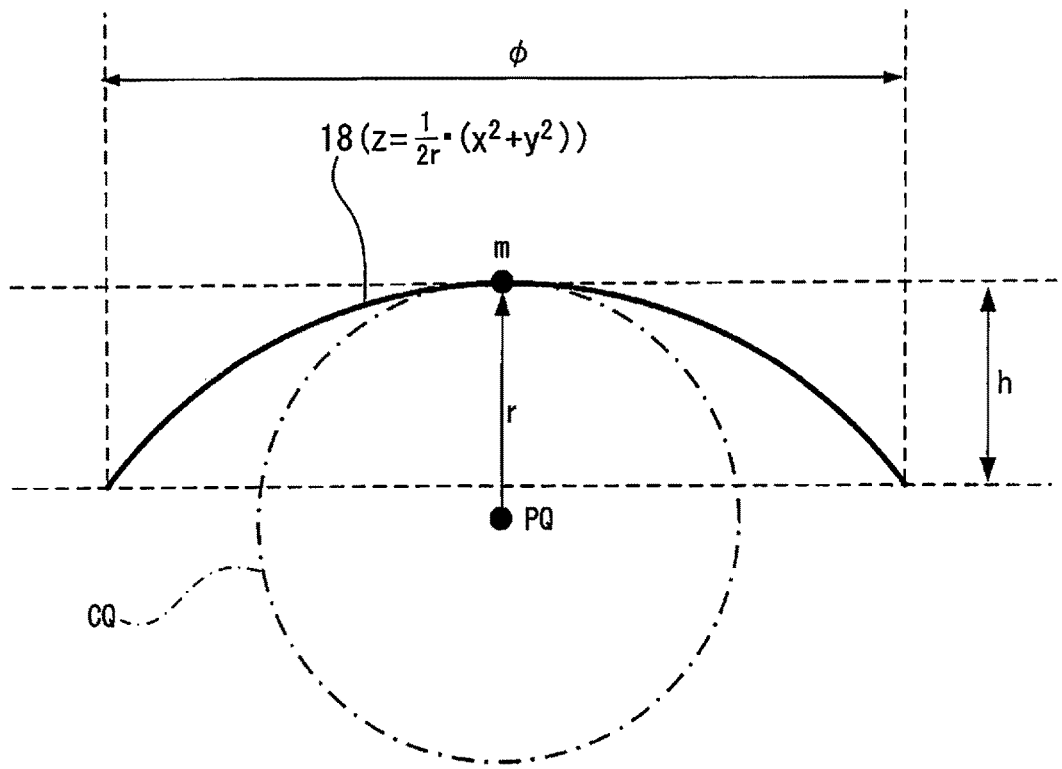
FIG. 17A is a drawing used to describe a reflecting surface including a part of a paraboloid (i.e., a paraboloid mirror)
Figure 17B:
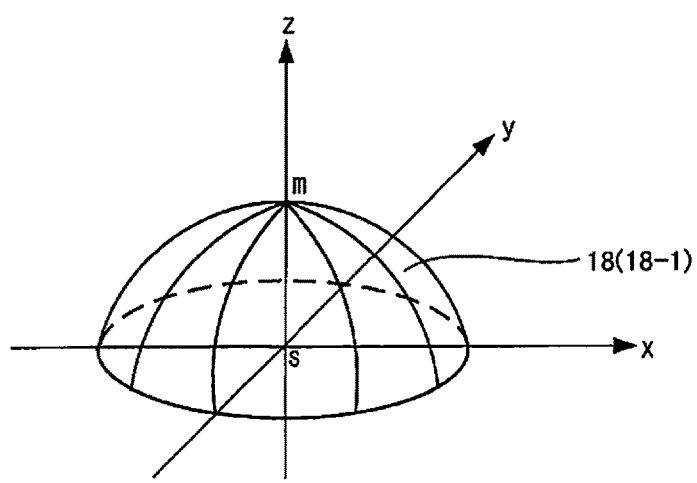
FIG. 17B is a drawing used to describe the reflecting surface including the part of the paraboloid (i.e., a paraboloid mirror)

FIGS. 17A and 17B are drawings used to describe a reflecting surface including a part of a paraboloid (i.e., a paraboloid mirror). As shown in FIG. 17B, when the z-axis among the mutually perpendicular x-, y-, and z-axes that define a 3-dimensional space is the optical axis (i.e., main optical axis), the paraboloid forming the reflecting surface may be a paraboloid of revolution having the z-axis as an axis of revolution. A point of intersection between the z-axis and the paraboloid of revolution is defined as an origin (surface origin) m.

In an instance in which r represents the curvature radius of a spherical surface CQ in contact with the origin m, the following Equation 3 is true with respect to the paraboloid of revolution, as shown in FIGS. 17A and 17B.

Mathematical Formula 3

$$z=(1/2r)\cdot(x^2+y^2) \quad (3)$$

The outer circumferential shape of the reflecting surface 18-1 with respect to the plan view is circular, as with the previous embodiment, and the diameter φ of the circle (i.e., the aperture diameter of the reflecting surface) is set to a predetermined value. When the aperture diameter φ of the reflecting surface is already known, the focal distance df of the reflecting surface and the curvature radius r of the spherical surface CQ in contact with the origin m of the paraboloid forming the reflecting surface have a one-to-one correspondence relationship. Therefore, when a preferable focal distance df is established, the curvature radius r of the spherical surface in contact with the origin m is established, and the paraboloid of revolution is unambiguously established by the above Equation 3. Also, since the aperture diameter φ of the reflecting surface is already known, a position at which the paraboloid of revolution is sliced along an x-y plane is thereby established, and the height h of the reflecting surface is unambiguously established. The three-dimensional shape (and height) of the reflecting surface is thereby unambiguously established.

Next, a behavior of directly reflected light (i.e., invalid light) in which the focal distance df of the reflecting surface 18-1 (i.e., a paraboloid mirror) is changed (with other parameters being fixed) will now be discussed with reference to FIGS. 18 through 20.

Figure 18:
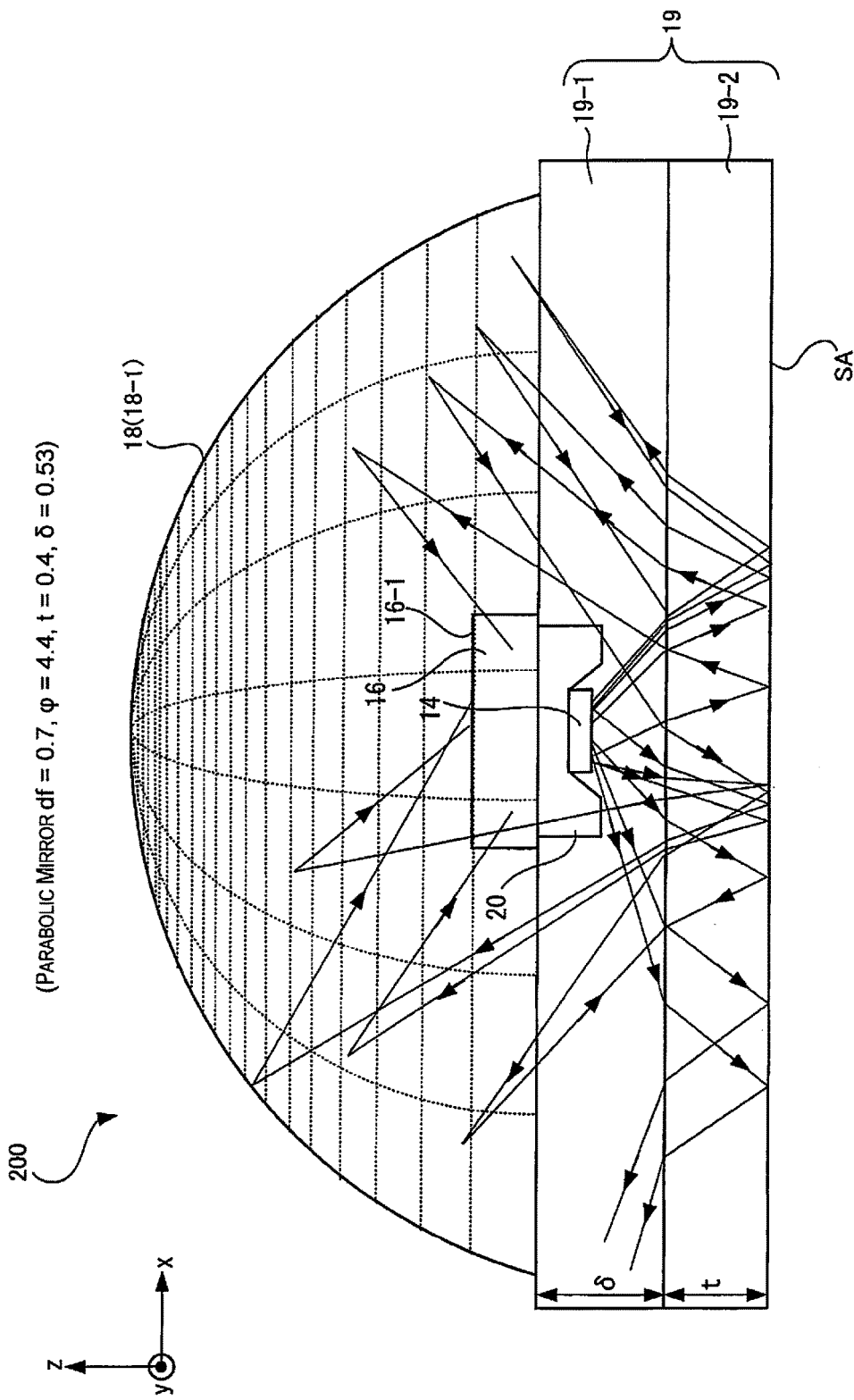
FIG. 18 is a drawing used to describe a behavior of directly reflected light when the focal distance df is 0.7 mm where the aperture diameter φ=4.4 mm, thickness t of contact member 19-2=0.4 mm, and height (spacing) δ of spacer member 19-1=0.53 mm.

FIG. 18 is a drawing used to describe a behavior of directly reflected light when the focal distance df is 0.7 mm where the aperture diameter φ=4.4 mm, the thickness t of contact member 19-2=0.4 mm, and the height (spacing) δ of the spacer member 19-1=0.53. The reflecting surface 18-1 of the reflecting part 18 shown in FIG. 18 includes a part of a paraboloid. In FIG. 18, the reflecting surface of the reflecting part 18 is shown, not as a cross-section, but as a shape having spatial depth (this also applies to subsequent drawings).

In FIG. 18, trajectories of directly reflected light (i.e., invalid light), produced by light emitted by the light-emitting part 14 (not including light reflected on the reflector or another member) reflecting on a side of the contact member 19-2 of the protecting part 19 towards the contact surface SA (i.e., the contact surface SA or a vicinity thereof) are shown by solid arrows.

As can be seen from FIG. 18, there is a high probability of once-reflected light, which is light emitted by the light-emitting part 14 reflecting once on the side of the contact member 19-2 towards the contact surface SA, being incident on the light-receiving region (i.e., the light-receiving surface) 16-1 of the light-receiving part 16. Specifically, there is a tendency towards a higher ratio of the amount of once-reflected incident light in relation to the total amount of light received at the light-receiving part 16.

Figure 19:
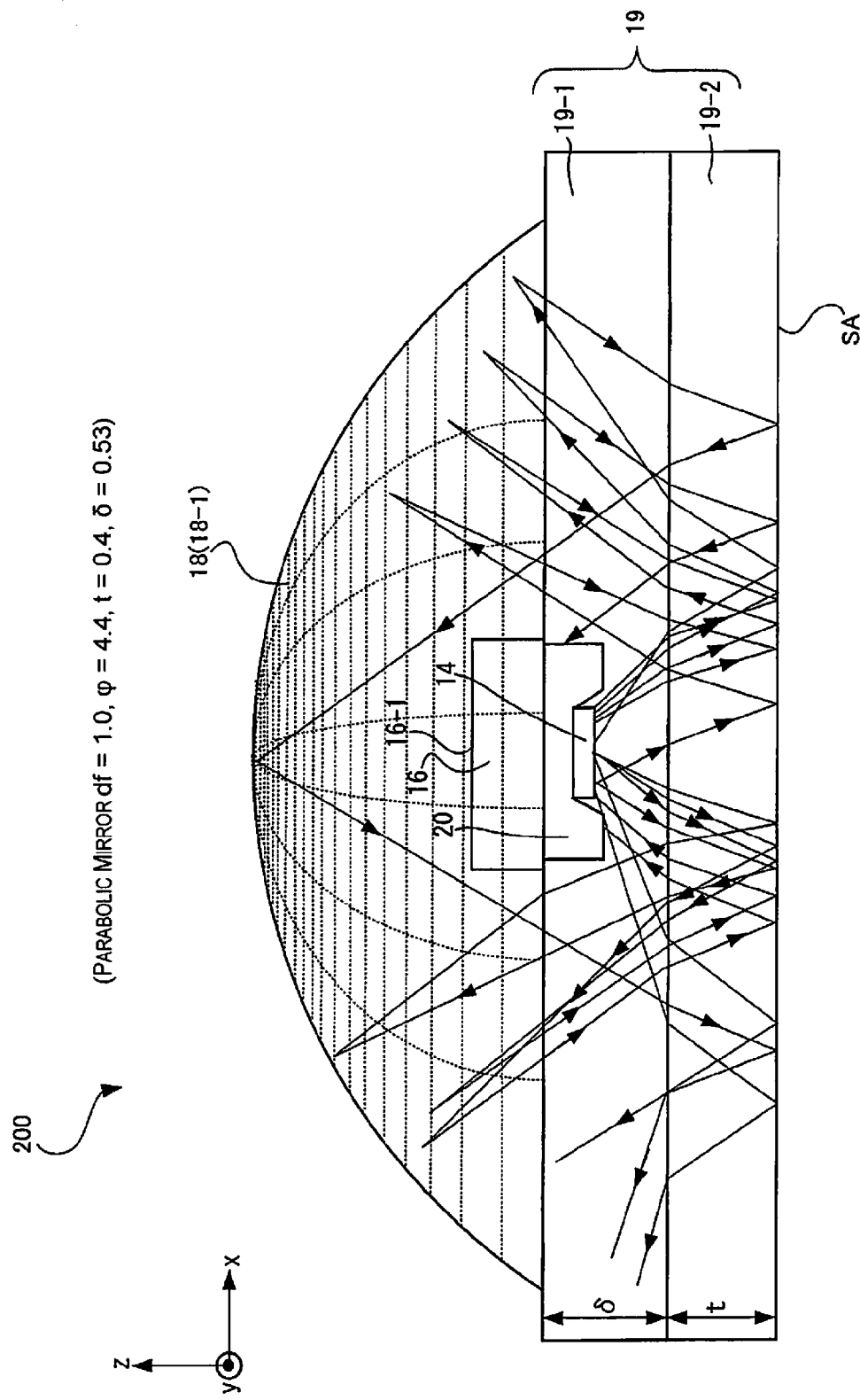
FIG. 19 is a drawing used to describe a behavior of directly reflected light when the focal distance df is 1.0 mm where the aperture diameter φ=4.4 mm, thickness t of contact member 19-2=0.4 mm, and height (spacing) δ of spacer member 19-1=0.53 mm.

FIG. 19 is a drawing used to describe a behavior of directly reflected light when the focal distance df is 1.0 mm where the aperture diameter φ=4.4 mm, the thickness t of the contact member 19-2=0.4 mm, and the height (spacing) δ of the spacer member 19-1=0.53.

As can be seen in FIG. 19, there are substantially no instances of once-reflected light, which is the light emitted by the light-emitting part 14 reflecting once on the side of the contact member 19-2 towards the contact surface SA, being incident on the light-receiving region (i.e., the light-receiving surface) 16-1 of the light-receiving part 16. There are also substantially no instances of twice-reflected light, which is the light emitted by the light-emitting part 14 reflecting twice on the side of the contact member 19-2 towards the contact surface SA, being incident on the light-receiving region (i.e., the light-receiving surface) 16-1 of the light-receiving part 16. Meanwhile, as with the example shown in FIG. 1A described above, reflected light from the blood vessel (i.e., valid reflected light having biological information) is incident on the light-receiving region (i.e., the light-receiving surface) 16-1 of the light-receiving part 16.

Figure 20:
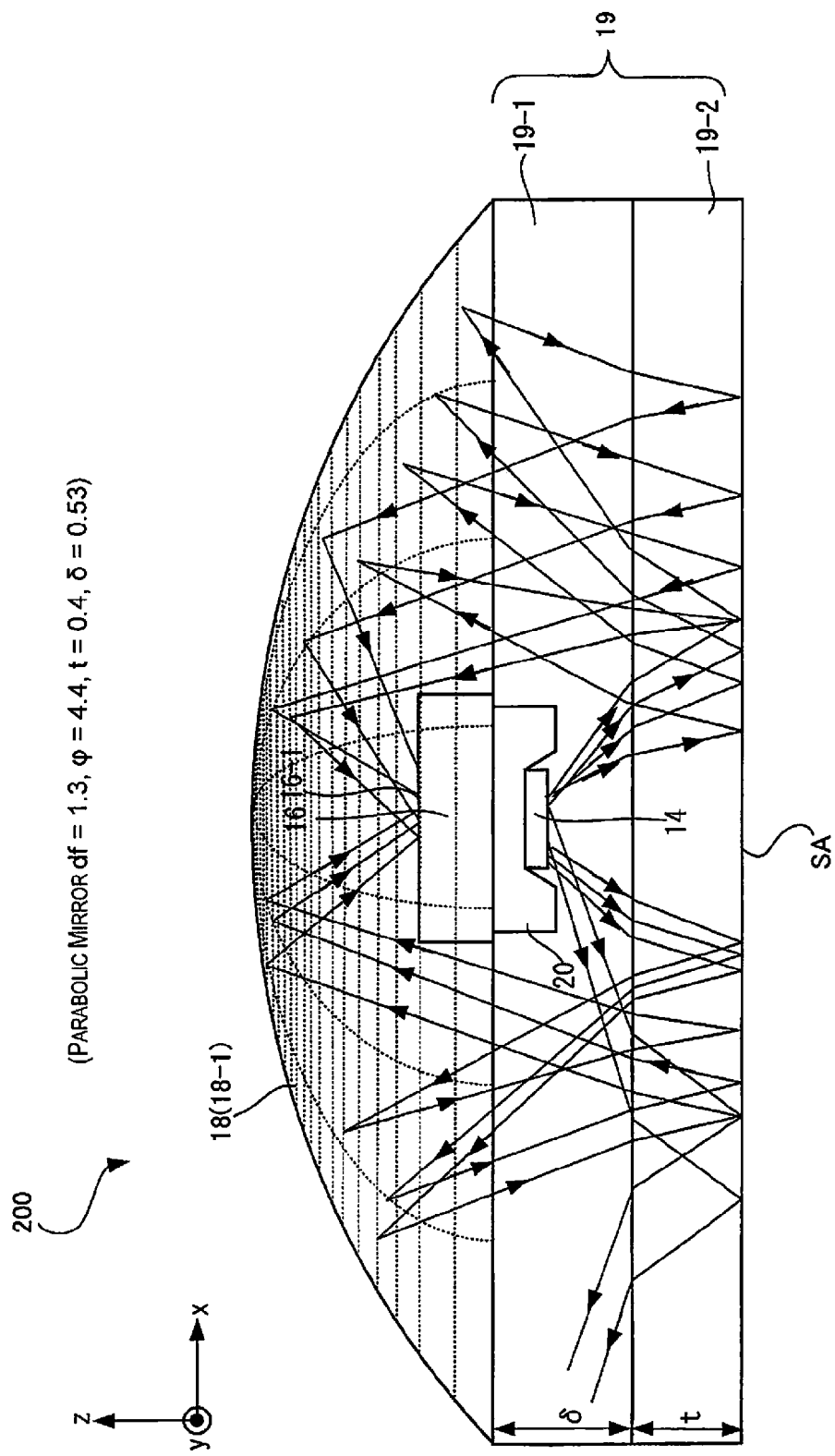
FIG. 20 is a drawing used to describe a behavior of directly reflected light when the focal distance df is 1.3 mm where the aperture diameter φ=4.4 mm, thickness t of contact member 19-2=0.4 mm, and height (spacing) δ of spacer member 19-1=0.53 mm.

FIG. 20 is a drawing used to describe a behavior of directly reflected light when the focal distance df is 1.3 mm where the aperture diameter φ=4.4 mm, the thickness t of the contact member 19-2=0.4 mm, and the height (spacing) δ of the spacer member 19-1=0.53.

As can be seen in FIG. 20, there is a high probability of the twice-reflected light, which is the light emitted by the light-emitting part 14 reflecting twice on the side of the contact member 19-2 towards the contact surface SA, being incident on the light-receiving region (i.e., the light-receiving surface) 16-1 of the light-receiving part 16. Specifically, there is a tendency towards a higher ratio of the amount of twice-reflected incident light in relation to the total amount of light received at the light-receiving part 16.

Figure 21:
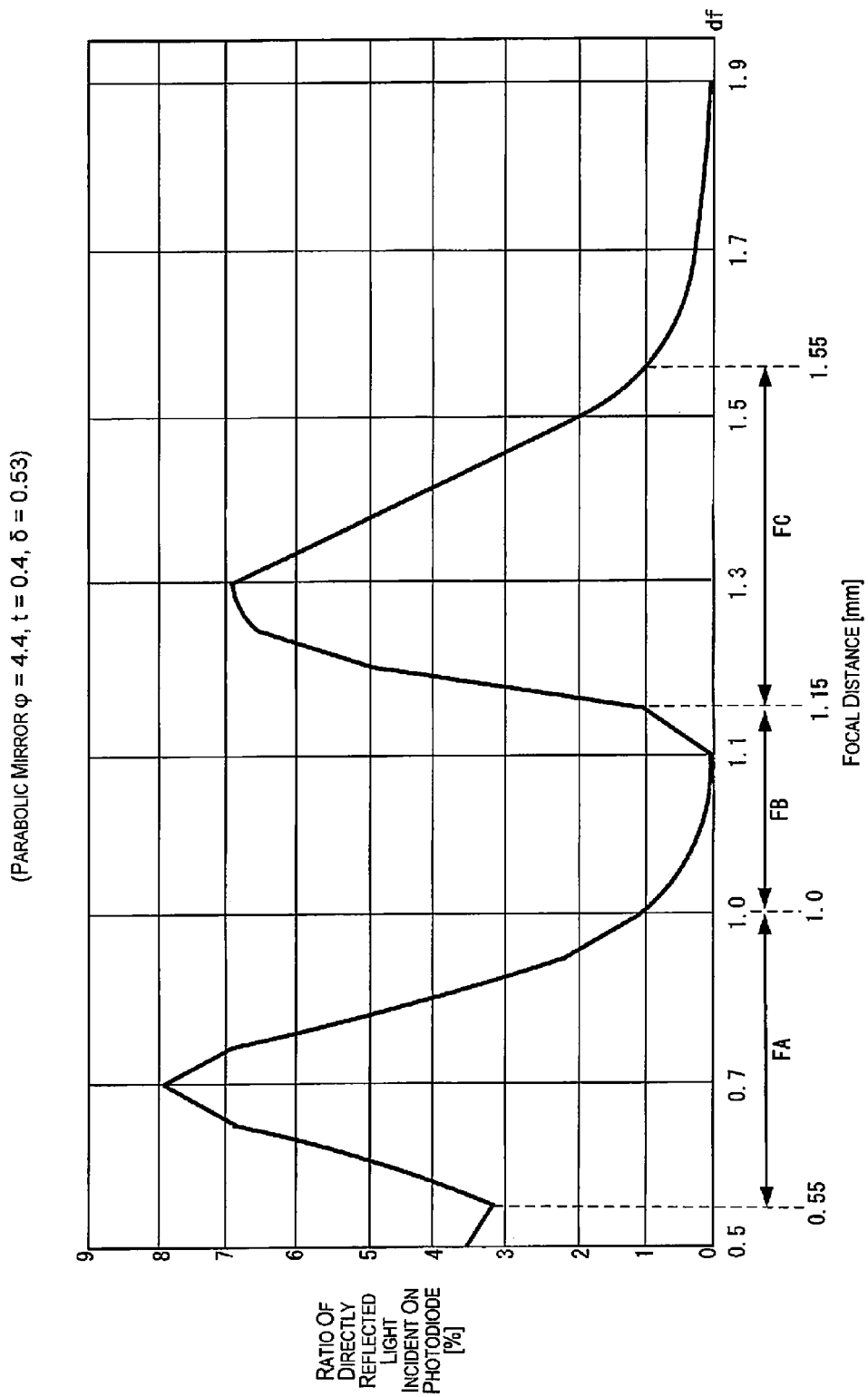
FIG. 21 is a drawing representing a change in the ratio (%) of the amount of directly reflected light incident on the light-receiving part (photodiode) in an instance in which the focal distance df is gradually increased where the aperture diameter φ=4.4 mm, t=0.4 mm, and δ=0.53 mm.

A simulation of a behavior of the directly reflected light was repeatedly performed, and a correlation between changes in the focal distance of the reflecting surface and the ratio of directly reflected light incident on the light-receiving part 16 was studied. A result is shown in FIG. 21. FIG. 21 is a drawing representing a change in the ratio (%) of the amount of directly reflected light incident on the light-receiving part (photodiode) in an instance in which the focal distance df is gradually increased where the aperture diameter φ=4.4 mm, t=0.4 mm, and δ=0.53 mm.

In FIG. 21, gradually increasing the focal distance df of the reflecting surface results first in a first focal distance range FA (i.e., a range of focal distance df from 0.55 mm to 1.0 mm), as with the above-described instance in which a reflecting surface including a part of a spherical surface is used. Next, a second focal distance range FB (i.e., a range of focal distance df from 1.0 mm to 1.15 mm) appears.

In the focal distance range FB, the ratio of the amount of directly reflected light incident on the light-receiving part is minimized so as to be equal to or below 1% (the first and second threshold values, used as predetermined threshold values in the present example to determine whether the amount of reflected light is high or low, are 1%). Also, the ratio of directly reflected light is almost zero in a vicinity of the focal distance df of 1.1.

Further increasing the focal distance df of the reflecting surface results in a third focal distance range FC (i.e., a range of focal distance df from 1.15 mm to 1.55 mm).

When such observations are taken into consideration, the focal distance of the reflecting surface (i.e., the paraboloid mirror) of the reflecting part 18 is preferably set within the second focal distance range FB, which is between the first focal distance range FA and the third focal distance range FC. The decrease in S/N of the detection signal outputted from the light-receiving part 16, caused by the directly reflected light (i.e., invalid light), is thereby minimized. As a result, the detection accuracy increases. Also, since the ratio of directly reflected light is almost zero in the vicinity of the focal distance df of 1.1, the focal distance is most preferably set in the vicinity of 1.1.

Also, although not shown, studying a change in S/N of the detection signal has confirmed that the amount of received valid light (i.e., valid reflected light) having biological information increases in the second focal distance range FB.

Therefore, setting the focal distance df within the second focal distance range makes it possible to increase the S/N of the detection signal corresponding to detection of the pulse rate as biological information. Specifically, improving the S/N of the detection signal makes it possible to perform detection with a higher degree of accuracy. In particular, setting the focal distance df to a value corresponding to a vicinity of the peak value of the S/N of the detection signal (i.e., 1.1) makes it possible to maximize the detection accuracy.

As described above, when the focal distance df of the reflecting surface is established, the three-dimensional shape and height of the reflecting surface are unambiguously established. Therefore, using the design method described above makes it possible to obtain a reflecting part 18 having preferable reflective characteristics with which the effect of directly reflected light can be reduced.

Third Embodiment

Figure 22:
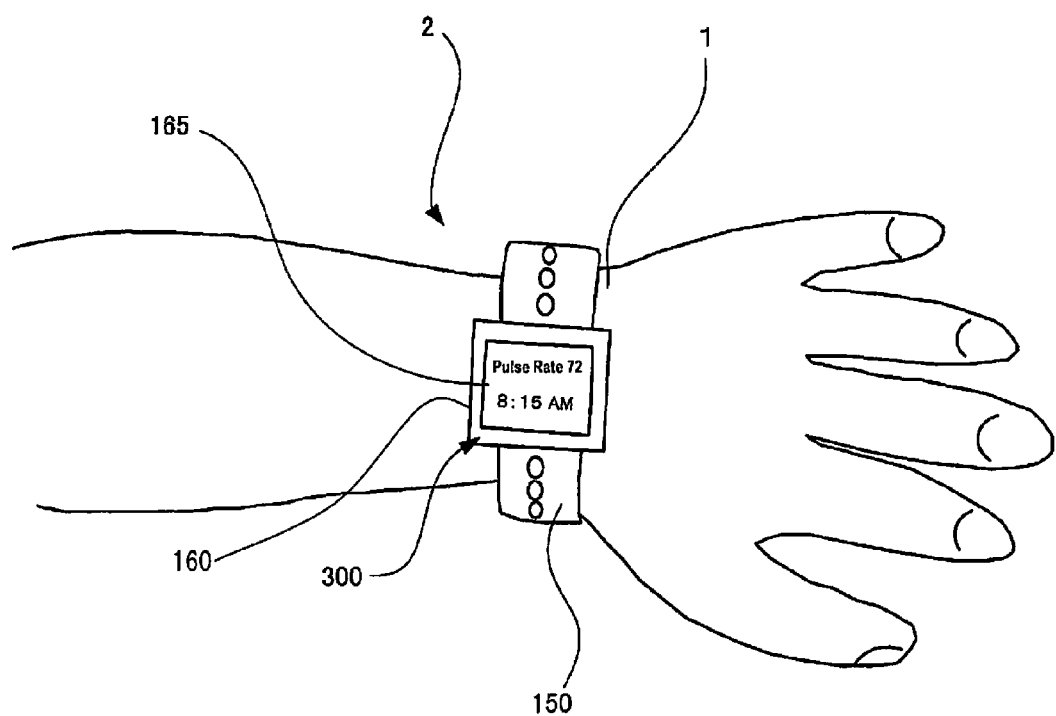
FIG. 22 is a drawing representing an external appearance of an example of a biological information measuring device (i.e., a wrist pulse rate monitor) including the biological information detector.

In the present embodiment, a description will be given for a biological information measuring device including the biological information detector. FIG. 22 is a drawing representing an external appearance of an example of a biological information measuring device (i.e., a wrist pulse rate monitor) including the biological information detector. The biological information measuring device 300 may further include a wristband 150 capable of attaching a housing member 160 for the biological information detector 200 to an arm (or specifically, a wrist), which is the detection site 1, of the test subject (i.e., human body) 2.

In the example shown in FIG. 22, the biological information is the pulse rate, and the pulse rate (i.e., "72"), which is a measurement result, is displayed on a display part 165 provided to the biological information measuring device 300. The biological information measuring device 300 also functions as a wristwatch. The time (e.g., "8:45 am") is displayed on the display part 165 provided to the biological information measuring device 300.

Although not shown, an opening part is provided to a back cover of the housing member 160 of the biological information measuring device 300 that also functions as the wristwatch, and the protecting part (i.e., protective case) 19 described above is exposed in the opening part.

Figure 23:
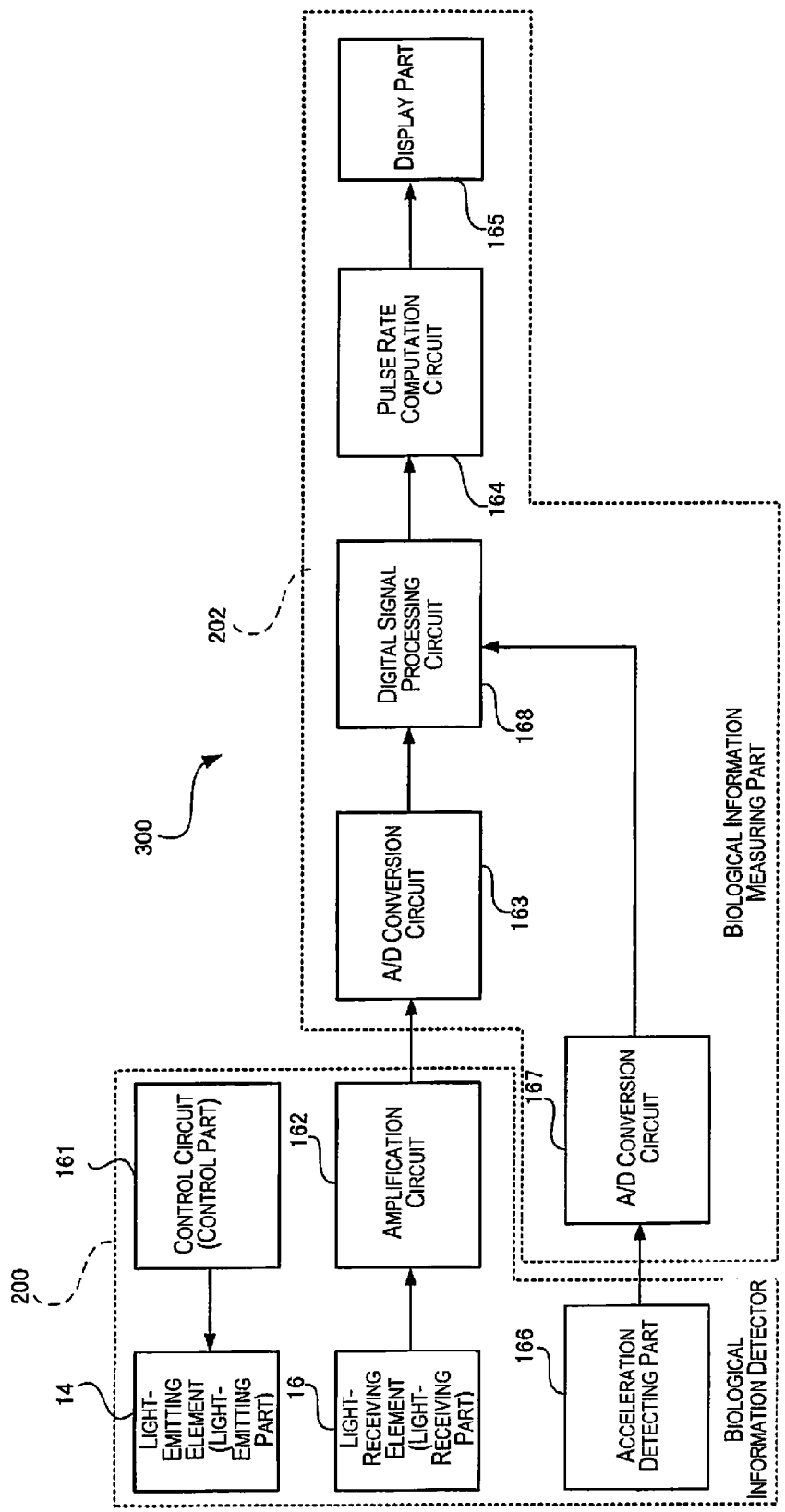
FIG. 23 is a drawing representing an example of an internal configuration of the biological information measuring device.

FIG. 23 is a drawing representing an example of an internal configuration of the biological information measuring device. The biological information measuring device 300 includes the biological information detector 200 shown in FIG. 1 and other drawings, and a biological information measuring part 202 for measuring biological information from a light reception signal generated by the light-receiving part 16 of the biological information detector. In FIG. 23, a portion that functions as a clock is omitted. The biological information detector 200 may have the light-emitting part 14, the light-receiving part 16, and a control circuit 161 for controlling the light-emitting part 14. The biological information detector 200 may further have an amplification circuit 162 for amplifying the light reception signal from the light-receiving part 16. The biological information detector 200 may further have an acceleration detecting part 166.

The biological information measuring part 202 may have an A/D conversion circuit 163 for performing A/D conversion of the light reception signal from the light-receiving part 16, and a pulse rate computation circuit 164 for computationally obtaining the pulse rate. The biological information measuring device 300 may further have the display part 165 for displaying the pulse rate.

As described above, the biological information detector 200 may have the acceleration detecting part 166; in such an instance, the biological information measuring part 202 may have an A/D conversion circuit 167 for performing A/D conversion on a detection signal from the acceleration detecting part 166, and a digital signal processing circuit 168 for processing a digital signal. The configuration of the biological information measuring device shown in FIG. 23 is given by way of example, but is not limited to the configuration shown.

The pulse rate computation circuit 164 may be, e.g., an MPU (i.e., a microprocessing unit) of an electronic device installed with the biological information detector 200. The control circuit 161 drives the light-emitting part 14. The control circuit 161 is, e.g., a constant current circuit, delivers a predetermined voltage (e.g. 6 V) to the light-emitting part 14 via a protective resistance, and maintains a current flowing to the light-emitting part 14 at a predetermined value (e.g. 2 mA). The control circuit 161 is capable of driving the light-emitting part 14 in an intermittent manner (e.g. at 128 Hz) in order to reduce consumption current. The control circuit 161 is formed on, e.g., a motherboard (not shown), and wiring between the control circuit 161 and the light-emitting part 14 is formed, e.g., on the substrate 11.

The amplification circuit 162 shown in FIG. 23 is capable of removing a DC component from the light reception signal (i.e., an electrical current) generated in the light-receiving part 16, extracting only an AC component, amplifying the AC component, and generating an AC signal. The amplification circuit 162 removes the DC component at or below a predetermined wavelength using, e.g., a high-pass filter, and buffers the AC component using, e.g., an operational amplifier. The light reception signal contains a pulsating component and a body movement component. The amplification circuit 162 and the control circuit 161 are capable of feeding a power supply voltage, for operating the light-receiving part 16 at, e.g., reverse bias, to the light-receiving part 16. In an instance in which the light-emitting part 14 is intermittently driven, the power supply to the light-receiving part 16 is also intermittently fed, and the AC component is also intermittently amplified. The amplification circuit 162 is formed on, e.g., the mother board (not shown), and wiring between the amplification circuit 162 and the light-receiving part 16 is formed on, e.g., the substrate 11. The amplification circuit 162 may also have an amplifier for amplifying the light reception signal at a stage prior to the high-pass filter. In an instance in which the amplification circuit 162 has an amplifier, the amplifier can be formed, e.g., on an end part of the substrate 11.

The A/D conversion circuit 163 converts an AC signal generated in the amplification circuit 162 into a digital signal (i.e., a first digital signal). The acceleration detecting part 166 detects, e.g., gravitational acceleration in three axes (i.e., x-axis, y-axis, and z-axis) and generates an acceleration signal. Movement of the body (i.e., the arm), and therefore the movement of the biological information measuring device, is reflected in the acceleration signal. The A/D conversion circuit 167 converts the acceleration signal generated in the acceleration detecting part 166 into a digital signal (i.e., a second digital signal).

The digital signal processing circuit 168 uses the second digital signal to remove or reduce the body movement component in the first digital signal. The digital signal processing circuit 168 may be formed by, e.g., an FIR filter or another adaptive filter. The digital signal processing circuit 168 inputs the first digital signal and the second digital signal into the adaptive filter and generates a filter output signal in which noise has been removed or reduced.

The pulse rate computation circuit 164 uses, e.g., fast Fourier transform (or in a broader sense, discrete Fourier transform) to perform a frequency analysis on the filter output signal. The pulse rate computation circuit 164 identifies a frequency that represents a pulsating component based on a result of the frequency analysis, and computationally obtains a pulse rate.

Using the wrist pulse rate monitor shown in FIG. 22 makes it possible to obtain, e.g., a time-series pulse rate information while the user performs jogging or another exercise. The obtained pulse rate information can be used in a versatile manner such as for improving the constitution of the user. However, situations such as the position of the wrist pulse rate monitor becoming displaced as a result of the exercise performed by the user, or the wrist pulse rate monitor being affected by external light, can be expected, and the number of factors that can reduce the detection accuracy (i.e., the measurement accuracy) is increased. Therefore, in order to secure a measurement that is as high as possible, it is preferable to take sufficient measures against the decrease in S/N due to light reflected near the surface of the contact member (i.e., light-transmitting member). In this respect, sufficient measures against directly reflected light (i.e., invalid light) have been implemented in the biological information detector 200 as described above. It is thereby possible to obtain a novel wrist pulse rate monitor that is capable of performing measurements with a high degree of accuracy.

Fourth Embodiment

In the present embodiment, a description will be given for a pulse oximeter as another example of the biological information measuring device 300. A biological information detector (i.e., an in-vivo probe) installed in the pulse oximeter can be obtained using a configuration that is identical to that in the previous embodiments (e.g., the configuration shown in FIGS. 1A and 2).

A description will be given based on the configuration shown in FIG. 1. The biological information detector 200 in the pulse oximeter includes the light-emitting part 14 and the light-receiving part 16. The light-emitting part 14 emits, e.g., a red light and infrared light. Reflected light, produced by the light emitted by the light-emitting part 14 reflecting at the detection site 1 (e.g., fingertip, arm, or wrist), is measured using the light-receiving part 16. Red-light and infrared absorbance of haemoglobin in the blood differ depending on presence of a bond with oxygen. Therefore, the arterial oxygen saturation ($S_pO_2$) can be measured by measuring the reflected light at the light-receiving part 16 and analyzing the reflected light.

Components that have been reflected by an artery or the like and components that have been reflected by a vein or soft tissue, which are included in all reflected light, can be distinguished from each other using the fact that pulsating components originate from arterial blood. It is also possible to count the pulse rate at the same time from pulsating pulse components.

The configuration of the biological information measuring part 202 for use in a pulse rate monitor shown in FIG. 23 can be used as a configuration of the biological information measuring part for use in the pulse oximeter. However, the pulse rate computation circuit 164 shown in FIG. 23 is replaced by an arterial oxygen saturation analysis circuit 164 in which a pulse rate computation circuit and an FFT or another approach is used.

According to one aspect of a biological information detector of the Embodiment, the biological information detector includes:

a light-emitting part;

a light-receiving part for receiving light having biological information, the light being emitted by the light-emitting part and reflected at a detection site of a test subject;

a reflecting part for reflecting the light having biological information;

a protecting part for protecting the light-emitting part, the protecting part having a contact member provided with a contact surface in contact with the detection site, the contact member being formed from a material that is transparent with respect to a wavelength of the light emitted by the light-emitting part; and a substrate arranged between the reflecting part and the protecting part, the light-emitting part being arranged on a first surface towards the protecting part, the light-receiving part being arranged on a second surface, opposite the first surface towards the reflecting part, and the substrate being formed from a material that is transparent with respect to the wavelength of the light emitted by the light-emitting part; wherein a once-reflected light, which is the light emitted from the light-emitting part being reflected once on a contact-surface side of the contact member, is inhibited from being incident on the light-receiving part.

According to the aspect described above, a component of the light emitted by the light-emitting part that is the once-reflected light (i.e., directly reflected light), which has reflected once on the contact-surface side of the contact member of the protecting part (i.e., the contact surface and a vicinity of the contact surface (including an interface between the contact surface and the detection site, as well as the skin surface and an inner side of the skin) of the contact member, which is a light-transmitting member) is inhibited from being incident on the light-receiving part.

Since the once-reflected light (i.e., directly reflected light; invalid light) is inhibited from being incident on the light-receiving part, it is possible to minimize a decrease in the S/N of a detection signal outputted from the light-receiving part.

According to another aspect of the biological information detector of the Embodiment, a twice-reflected light, which is the light emitted from the light-emitting part reflected twice on the contact-surface side of the contact member, is inhibited from being incident on the light-receiving part.

According to the aspect described above, a component of the light emitted by the light-emitting part that is the twice-reflected light produced by a double reflection on the contact-surface side of the contact member of the protecting part (i.e., the contact surface and a vicinity of the contact surface of the contact member, which is a light-transmitting member) is inhibited from being incident on the light-receiving part.

Since the twice-reflected light (i.e., directly reflected light; invalid light) is inhibited from being incident on a light-receiving region of the light-receiving part, it is possible to minimize a decrease in the S/N of the detection signal outputted from the light-receiving part.

According to another aspect of the biological information detector of the Embodiment, the reflecting part has a reflecting surface including a part of a spherical surface; the diameter of an outer circumferential circle of the reflecting part with respect to a plan view is set at a predetermined value; and in an instance in which there exist, as ranges of a focal distance of the reflecting part, a first focal distance range, in which a ratio of a once-reflected incident light, which is the once-reflected light reflecting on the reflecting surface and being incident on the light-receiving part, with respect to a total amount of received light is higher than a first threshold value; a second focal distance range; and a third focal distance range, in which a ratio of a twice-reflected incident light, which is the twice-reflected light reflecting on the reflecting surface and being incident on the light-receiving part, with respect to the total amount of received light is higher than a second threshold value; the focal distance of the reflecting surface is set within the second focal distance range, which is between the first focal distance range and the third focal distance range.

The reflecting part has a reflecting surface, and the reflecting surface includes a part of a spherical surface, which is a quadric surface. The reflecting surface has an outer circumferential shape that is circular with respect to a plan view, and the diameter (i.e., the aperture diameter of the reflecting surface) of the circle (i.e., the outer circumferential circle of the reflecting surface) is set to a predetermined value.

According to the present aspect, changing the focal distance of the reflecting surface so as to, e.g., gradually increase results first in a focal distance range in which a ratio of light that is the once-reflected light, which has reflected once on a contact-surface side of the contact member, reflecting again at the reflecting surface and being incident on the light-receiving part (i.e., the once-reflected incident light), with respect to a total amount of light received at the light-receiving part, is higher than a predetermined threshold value (i.e., the first threshold value). This focal distance range is defined as the first focal distance range.

Further increasing the focal distance of the reflecting surface results next in a focal distance range in which almost no directly reflected light (i.e., once-reflected light and twice-reflected light) reaches the light-receiving part. This focal distance range is defined as the second focal distance range.

Further increasing the focal distance of the reflecting surface results in a focal distance range in which a ratio of light that is the twice-reflected light, which has reflected twice on the contact-surface side of the contact member, reflecting again at the reflecting surface and being incident on the light-receiving part (i.e., the twice-reflected incident light), in relation to the total amount of light received at the light-receiving part, is higher than a predetermined threshold value (i.e., the second threshold value). This focal distance range is defined as the third focal distance range. The first threshold value and the second threshold value may be identical or may differ from each other.

Based on the above observation, according to the aspect described above, the focal distance of the reflecting surface of the reflecting part is set within the second focal distance range, which is between the first focal distance range and the third focal distance range. Once the focal distance of the reflecting surface is established, the curvature radius of the spherical surface forming the reflecting surface is established (the curvature radius is twice the length of the focal distance). The spherical surface is thereby unambiguously established. The aperture diameter of the reflecting surface is already known. This means that a position at which the spherical surface is sliced along, e.g., an x-y plane is unambiguously established. A three-dimensional shape (and height) of a reflecting surface including a part of the spherical surface is thereby established.

According to the aspect described above, the once-reflected light (i.e., directly reflected light; invalid light) and the twice-reflected light (i.e., directly reflected light; invalid light) are inhibited from being incident on the light-receiving part. It is thereby possible to reduce the effect of light reflected on the contact-surface side of the contact member (e.g., a decrease in the S/N of the detection signal outputted from the light-receiving part).

According to another aspect of the biological information detector of the Embodiment, the following relationship is true, given that $\phi$ represents the diameter of the outer circumferential circle of the reflecting part; r represents the curvature radius of the spherical surface forming the reflecting surface; h represents the height of the reflecting surface, the height h being established in correspondence with the curvature radius r and the diameter $\phi$ of the outer circumferential circle of the reflecting part and representing a distance between the second surface and a point of intersection between an optical axis and the reflecting surface; and $\Delta h$ represents a difference between the height h of the reflecting surface and the curvature radius r of the reflecting surface.

Mathematical formula 4

$$r = \sqrt{\{\Delta h^2 + (\phi/2)^2\}} \qquad (4)$$

The aspect described above defines the curvature radius r of the spherical surface forming the reflecting surface. Specifically, given that $\phi$ represents the aperture diameter of the reflecting surface, h represents the height of the reflecting surface established in correspondence with the aperture diameter $\phi$ and the curvature radius r of the spherical surface forming the reflecting surface, and $\Delta h$ represents the difference between the height h of the reflecting surface and the curvature radius r of the reflecting surface, the curvature radius r is represented by the above Equation (4).

In an instance in which the aperture diameter $\phi$ of the reflecting surface is already known, when, for example, the focal distance df of the reflecting part is changed, the curvature radius r of the spherical surface forming the reflecting surface changes. When the curvature radius r changes, the difference Δh between the height h and the curvature radius r of the reflecting surface changes. The difference Δh and the focal distance df of the spherical surface forming the reflecting surface have a one-to-one correspondence relationship; when the focal distance df increases, the difference Δh also increases. When the focal distance df of the reflecting part is established, the difference Δh is established, and due to the Pythagorean theorem, the above Equation 4 is established. Therefore, when a preferred focal distance of the reflecting surface is established, it is possible to use the above Equation 4 to unambiguously establish the curvature radius r of the reflecting surface, whereby the spherical surface forming the reflecting surface is established. Since the aperture diameter of the reflecting surface is already known, the three-dimensional shape and the height of the reflecting surface are unambiguously established.

According to the aspect described above, it is thereby possible to obtain a reflecting part having a reflecting surface designed so that the effect of light reflected on the contact-surface side of the contact member (e.g., a decrease in the S/N of the detection signal outputted from the light-receiving part) can be reduced (e.g., through optimization design).

According to another aspect of the biological information detector of the Embodiment, the reflecting part has a reflecting surface including a part of a paraboloid;

the paraboloid is a paraboloid of revolution having a z-axis as an axis of revolution, when a z-axis, among a mutually perpendicular x-axis, a y-axis, and the z-axis, is an optical axis;

the following relationship:
Mathematical formula 5

$$z=(1/2r)\cdot(x^2+y^2) \qquad (5)$$

is established with regards to the paraboloid of revolution when an origin is defined as a point of intersection between the z-axis and the paraboloid of revolution and r is defined as the curvature radius of the spherical surface in contact with the origin;

the diameter of an outer circumferential circle of the reflecting part with respect to the plan view is set to a predetermined value; and in an instance in which there exist, as ranges of a focal distance of the reflecting part, a first focal distance range, in which a ratio of a once-reflected incident light, which is the once-reflected light reflecting on the reflecting surface and being incident on the light-receiving part, with respect to a total amount of received light is higher than a predetermined threshold value (i.e., a first threshold value);

a second focal distance range; and a third focal distance range, in which a ratio of a twice-reflected incident light, which is the twice-reflected light reflecting on the reflecting surface and being incident on the light-receiving part, with respect to the total amount of received light is higher than a predetermined threshold value (i.e., a second threshold value), the focal distance of the reflecting surface is set within the second focal distance range, which is between the first focal distance range and the third focal distance range.

According to the aspect described above, a paraboloid is used as a quadric surface that forms the reflecting surface of the reflecting part. A paraboloid of revolution can be used as the paraboloid. The paraboloid of revolution is a quadric surface obtained by revolving a parabola, using the z-axis, which is an axis of symmetry, as an axis of revolution, where the z-axis among the mutually perpendicular x-, y-, and z-axes that define a 3-dimensional space is the optical axis (i.e., a curved surface represented by a quadratic equation with three unknowns of x, y, and z). When the origin (i.e., a surface origin) is defined as the point of intersection between the z-axis and the paraboloid of revolution and r is defined as the curvature radius of the spherical surface in contact with the origin, the paraboloid of revolution can be represented by the above Equation 5.

In an instance in which the aperture diameter φ of the reflecting surface is already known, the focal distance df of the reflecting surface and the curvature radius r of the spherical surface in contact with the origin of the paraboloid forming the reflecting surface, for example, have a one-to-one correspondence relationship. Therefore, when a preferred focal distance df is established, the curvature radius r of the spherical surface in contact with the origin is established, and the shape of the paraboloid of revolution is unambiguously established by the above Equation 5. Also, since the aperture diameter of the reflecting surface is already known, a position at which the paraboloid of revolution is sliced along an x-y plane is thereby established. The three-dimensional shape and height of the reflecting surface including the paraboloid are thereby unambiguously established.

In an instance in which a reflecting surface including a part of a paraboloid of revolution is used, as with the instance described above in which a reflecting surface including a part of a spherical surface is used, when the focal distance df is gradually increased, first, the first focal distance range appears, then the second focal distance range appears, then the third focal distance range appears. In the aspect described above, the focal distance of the reflecting surface provided to the reflecting part is set within the second focal distance range, which is between the first focal distance range and the third focal distance range. As described above, when the focal distance of the reflecting surface is established, the three-dimensional shape and height of the reflecting surface are unambiguously established. According to the aspect described above, the reflecting part having, e.g., the reflecting surface that is optimized can thereby be obtained. The aspect described above thereby makes it possible to obtain the reflecting part having the reflecting surface that is, e.g., optimized and that makes it possible to reduce the effect of light reflected on the contact-surface side of the contact member (e.g., a decrease in the S/N of the detection signal outputted from the light-receiving part).

According to one aspect of the biological information measuring device of the Embodiment, there is provided a biological information measuring device including the biological information detector according to any of the above-mentioned aspects, and a biological information measuring part for measuring the biological information according to a detection signal outputted from the light-receiving part.

The biological information detector according to any of the above aspects are designed so as to be capable of reducing the effect of light reflected on the contact-surface side of the contact member (e.g., a decrease in the S/N of the detection signal outputted from the light-receiving part). The biological information measuring device provided with the biological information detector is thereby capable of measuring biological information to a high degree of accuracy. Specific examples of the biological information measuring device include a pulse rate monitor, a sphygmograph, and a pulse oximeter for measuring arterial oxygen saturation (SpO2).

According to another aspect of the biological information measuring device of the Embodiment, there is provided a biological information measuring device in which the biological information is a pulse rate. In the aspect described above, the biological information measuring device is a pulse rate monitor. The blood vessel that is a biological information source is located within subcutaneous tissue located at the detection site (e.g., a finger, arm, or wrist). Light emitted from the light-emitting part provided to the pulse rate monitor reaches a blood vessel and is reflected; a portion of the light also being partially absorbed at the blood vessel. Due to an effect of the pulse, the rate of absorption at the blood vessel varies, and the amount of light reflected at the blood vessel (i.e., light reflected at the detection site) also varies in correspondence with the pulse. Therefore, the light reflected at the blood vessel contains pulse rate information as biological information. The pulse rate can therefore be measured according to a biological information detection signal outputted from the light-receiving part (including a pulsating component corresponding to the pulse).

The biological information measuring device may have a wristband capable of attaching the biological information detector to, e.g., a wrist (or an arm) of the test subject, and, e.g., a wrist pulse rate monitor (or a wrist sphygmograph) is thereby realized. Using a wrist pulse rate monitor makes it possible to obtain, e.g., a time-series pulse rate information while the user performs jogging or another exercise. The obtained pulse rate information can be used in a versatile manner such as for improving the constitution of the user. However, situations such as the position of the wrist pulse rate monitor becoming displaced as a result of the exercise performed by the user, or the wrist pulse rate monitor being affected by external light, can be expected, and the number of factors that can reduce the detection accuracy (i.e., the measurement accuracy) is increased. Therefore, in order to secure a highly accurate measurement, it is preferable to take sufficient measures against the decrease in S/N due to light reflected near the surface of the contact member (i.e., light-transmitting member) to increase the S/N as much as possible. In this respect, the biological information detector according to any of the above aspects is designed so as to be capable of reducing the effect of light reflected on the contact-surface side of the contact member (e.g., a decrease in the S/N of the detection signal outputted from the light-receiving part) as described above; therefore, the pulse rate monitor according to the aspect described above is capable of detecting the pulse rate to a high degree of accuracy and at a high sensitivity, and can be readily applied to a wrist pulse rate monitor.

A method for designing a reflecting part of a biological information detector of another aspect of the Embodiment includes: the biological information detector having: a light-emitting part; a light-receiving part for receiving light having biological information, the light being emitted by the light-emitting part and reflected at a detection site of a test subject; a reflecting part having a reflecting surface for reflecting the light having biological information, the reflecting surface including a part of a spherical surface or a part of a paraboloid, wherein the diameter of an outer circumferential circle of the reflecting surface with respect to the plan view is set to a predetermined value; a protecting part having a contact member provided with a contact surface in contact with the detection site, the contact member being formed from a material that is transparent with respect to a wavelength of the light emitted by the light-emitting part, and protecting the light-emitting part; and a substrate arranged between the reflecting part and the protecting part, the light-emitting part being arranged on a first surface towards the protecting part, the light-receiving part being arranged on a second surface, opposite the first surface and towards the reflecting part, and the substrate being formed from a material that is transparent with respect to the wavelength of the light emitted by the light-emitting part; determining, while changing the focal distance of the reflecting surface, a first focal distance range, in which a ratio of a once-reflected incident light with respect to a total amount of received light is higher than a first threshold value. The once-reflected incident light being a once-reflected light having reflected once on the contact-surface side of the contact member reflecting on the reflecting surface and being incident on a light-receiving region of the light-receiving part; determining, while changing the focal distance of the reflecting surface, a third focal distance range, in which a ratio of a twice-reflected incident light with respect to a total amount of received light is higher than a second threshold value, the twice-reflected incident light being a twice-reflected light having reflected twice on the contact-surface side of the contact member reflecting on the reflecting surface and being incident on a light-receiving region of the light-receiving part; and setting the focal distance of the reflecting surface in a second focal distance range between the first focal distance range and the third focal distance range.

The aspect described above shows a preferred method for designing the reflecting part of the biological information detector. The biological information detector has the reflecting part. The reflecting part has the reflecting surface, and the reflecting surface includes a part of a quadric surface. In the aspect described above, the reflecting surface includes a part of a spherical surface or a part of a paraboloid. The outer circumferential shape of the reflecting surface is circular with respect to the plan view. For example, when the z-axis among the mutually perpendicular x-, y-, and z-axes that define a 3-dimensional space is the optical axis, the outer circumferential shape of a cross-section surface formed by slicing the spherical surface along an x-y plane is circular, and the diameter of the circle (i.e., the aperture diameter of the reflecting surface) is set to a predetermined value.

The behavior of the ratio of incident light corresponding to directly reflected light that is reflected on the contact-surface side (i.e., contact surface and a vicinity of the contact surface) of the contact member (i.e., a light-transmitting member) and is incident on the light-receiving part, with respect to the total amount of light received at the light-receiving part, is then examined while changing the focal distance of the reflecting surface.

Changing the focal distance of the reflecting surface so as to, e.g., gradually increase, results first in a focal distance range in which a ratio of light that is the once-reflected light, which has reflected once on the contact-surface side of the contact member, reflecting again at the reflecting surface and being incident on the light-receiving part (i.e., the once-reflected incident light), with respect to a total amount of light received at the light-receiving part, is higher than a predetermined threshold value (i.e., the first threshold value). This focal distance range is defined as the first focal distance range.

Further increasing the focal distance of the reflecting surface results next in a focal distance range in which almost no directly reflected light (i.e., once-reflected light and twice-reflected light) reaches the light-receiving part. This focal distance range is defined as the second focal distance range.

Further increasing the focal distance of the reflecting surface results in a focal distance range in which a ratio of light that is the twice-reflected light, which has reflected twice on the contact-surface side of the contact member, reflecting again at the reflecting surface and being incident on the light-receiving part (i.e., the twice-reflected incident light), in relation to the total amount of light received at the light-receiving part, is higher than a predetermined threshold value (i.e., the second threshold value). This focal distance range is defined as the third focal distance range.

The focal distance of the reflecting surface of the reflecting part is set within the second focal distance range, which is between the first focal distance range and the third focal distance range. Once the focal distance of the reflecting surface is established, the three-dimensional shape and height of the reflecting surface are unambiguously established.

According to the aspect described above, it is possible to efficiently design a reflecting surface (i.e., a reflecting part) having preferable reflective characteristics, capable of minimizing incidence of the once-reflected light (i.e., directly reflected light; invalid light) and the twice-reflected light (i.e., directly reflected light; invalid light) on the light-receiving part.

According to the embodiment described above, it is possible to reduce an effect of directly reflected light when biological information is being detected.

A biological information detector according to the embodiment includes a light-emitting part, a reflecting part, a light-receiving part, a protecting part, and a processing part. The reflecting part has a curve shaped reflecting surface that is configured to reflect light emitted by the light-emitting part. The light-receiving part is configured to receive incident light that is emitted by the light-emitting part and reflected at a detection site of a user. The protecting part is configured to protect the light-emitting part, and the protecting part haw a contact surface adapted to contact with the detection site. The processing part is configured to process a light reception signal outputted from the light-receiving part. The light-emitting part has a light-emitting surface substantially in parallel to the contact surface, and a distance between the light-emitting surface and the contact surface is within a range of 0.4 mm to 0.9 mm According to the embodiment, the protecting part is formed from a material that is transparent with respect to a wavelength of the light emitted by the light-emitting part.

According to the embodiment, the light emitted by the light-emitting part is green in color and has a peak intensity within a wavelength range of 425 nm to 625 nm.

The biological information detector according to the embodiment further comprises a substrate supporting the light-emitting part, the light-receiving part and the reflecting part, and the substrate is in contact with the protecting part. At least a part of the substrate is coated with a transmitting material that transmits the light emitted by the light-emitting part.

The biological information detector according to the embodiment further comprises an acceleration sensor configured to detect acceleration generated by the user and to output an acceleration signal to the processing part to remove or reduce a body movement component in the digital signal outputted from the light-receiving part.

The biological information detector according to the embodiment further comprises a first A/D converter configured to convert the light reception signal from the light-receiving part into a first digital signal, and a second A/D converter configured to convert the acceleration signal from the acceleration sensor into a second digital signal. The processing part generates the biological information using the first digital signal and the second digital signal.

Although a detailed description was given above concerning preferred embodiments of the inventions, persons skilled in the art should be able to easily understand that various modifications can be made to the invention. Accordingly, all of such examples of modifications are to be included in the scope of the invention. For example, terms stated at least once together with different terms having broader sense or identical sense in the specification or drawings may be replaced with those different terms in any and all locations of the specification or drawings.

What is claimed is:

1. A biological information detector comprising:
    a wristband adapted to be attached to a wrist of a user;
    a housing connected to the wristband and adapted to be placed on the wrist of the user;
    an opening defined in a surface of the housing adapted to face a surface of the wrist of the user;
    a light-emitting part disposed inside the housing and configured to emit green light;
    a reflecting part disposed in periphery of the light emitting part, and configured to reflect the light emitted by the light-emitting part, wherein the reflecting part is disposed inside the housing;
    a light-receiving part disposed inside the housing, and configured to receive reflected light reflected at a detection site of the wrist of the user; and
    a protecting part configured to protect the light-emitting part and the reflecting part, and is disposed at the opening of the housing to contact with the detection site with the protecting part being disposed between the light-emitting part and the detection site, the protecting part being made of a material that is transparent with respect to a wavelength of the light emitted by the light-emitting part, the protecting part including a first surface and a second surface, the first surface being configured to contact the surface of the wrist of the user, the second surface being disposed between the first surface and the light-emitting part, a thickness of a part of the protecting part that overlaps the light-emitting part in a plan view being a uniform thickness, and the first surface and the second surface being flat surfaces.

2. The biological information detector according to claim 1, wherein
    the reflecting part has a protruding part which protrude toward the detection site and has a inclined surface which reflects the light emitted by the light-emitting part.

3. The biological information detector according to claim 1, wherein
    the light emitted by the light-emitting part has a peak intensity within a wavelength range of 425 nm to 625 nm.

4. The biological information detector according to claim 1, wherein
    the protecting part has a member which protrudes toward the detection site from the housing.

5. The biological information detector according to claim 1, further comprising:

an acceleration sensor disposed inside the housing member, and configured to detect an acceleration signal generated from a motion of the user;

a first A/D converter configured to convert the light reception signal from the light-receiving part into a first digital signal; and a second A/D converter configured to convert the acceleration signal from the acceleration sensor into a second digital signal.

6. The biological information detector according to claim 5, further comprising:

a processing part disposed inside the housing, and configured to calculate a pulse rate using a light-reception signal outputted by the light-receiving part.

7. The biological information detector according to claim 6, wherein the processing part calculates the pulse rate using the first digital signal and the second digital signal.

8. The biological information detector according to claim 1, wherein the light-emitting part is configured to be driven intermittently.

9. The biological information detector according to claim 1, wherein the protecting part is spaced apart from the light-emitting part.

* * * * *